United States Patent
Kolesky et al.

(10) Patent No.: US 11,654,121 B1
(45) Date of Patent: May 23, 2023

(54) COMBINATION THERAPIES FOR THE TREATMENT OF VIRAL INFECTIONS

(71) Applicant: Flagship Pioneering Innovations VI, LLC, Cambridge, MA (US)

(72) Inventors: David Barry Kolesky, Arlington, MA (US); Michael Ka Chun Wong, Arlington, MA (US); Hok Hei Tam, Newton, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 17/878,469

(22) Filed: Aug. 1, 2022

Related U.S. Application Data

(60) Provisional application No. 63/394,030, filed on Aug. 1, 2022, provisional application No. 63/354,490, filed on Jun. 22, 2022.

(51) Int. Cl.
| | |
|---|---|
| *A01N 43/04* | (2006.01) |
| *A61K 31/70* | (2006.01) |
| *A61K 31/122* | (2006.01) |
| *A61P 31/14* | (2006.01) |
| *A61K 31/706* | (2006.01) |

(52) U.S. Cl.
CPC .......... *A61K 31/122* (2013.01); *A61K 31/706* (2013.01); *A61P 31/14* (2018.01)

(58) Field of Classification Search
None
See application file for complete search history.

(56) References Cited

FOREIGN PATENT DOCUMENTS

WO    2021/224382 A1    11/2021

OTHER PUBLICATIONS

Jang, Woo Dae, et al. "Drugs repurposed for COVID-19 by virtual screening of 6,218 drugs and cell-based assay." Proceedings of the National Academy of Sciences 118.30 (2021): e2024302118.*
Hillen et al., "Structure of replicating SARS-CoV2 polymerase" Nature, 2020, vol. 584, pp. 154-156.
Matos et al., "Identification of hypericin as a candidate repurposed therapeutics agent for Covid-19 and its potentional anti-SARS-CoV-2 activity" Frontiers in Microbiology, 2022, vol. 13, pp. 1-11.

* cited by examiner

*Primary Examiner* — Patrick T Lewis
(74) *Attorney, Agent, or Firm* — Lando & Anastasi, LLP

(57) ABSTRACT

The present disclosure relates to therapeutic agents and combinations thereof (e.g., pharmaceutical compositions) for the treatment of a viral infection in a subject, tissue or cell.

18 Claims, 3 Drawing Sheets

COMBINATION THERAPIES FOR THE TREATMENT OF VIRAL INFECTIONS

CROSS-REFERENCE TO RELATED APPLICATIONS

This application claims priority to U.S. Provisional Application No. 63/354,490, filed on Jun. 22, 2022 and U.S. Provisional Application No. 63/394,030 filed Aug. 1, 2022, the entire contents of which is hereby incorporated by reference.

BACKGROUND

Small molecule antiviral agents are a diverse class of antiviral therapies, approved for treatment of many viral infections including hepatitis B, hepatitis C, influenza, herpes simplex-1, and HIV. Despite their efficacy, these compounds may often present harmful side effects resulting from toxicity. As such, there exists a need to improve the clinical profile of many antiviral agents.

SUMMARY

The present disclosure relates to therapeutic agents and combinations thereof (e.g., pharmaceutical compositions) for the treatment of a viral infection in a subject, tissue or cell. In one aspect, the present disclosure features a method of treating a viral infection (e.g., a coronavirus infection, e.g., Covid-19) in a subject comprising administering a combination of a hypericin compound and an antiviral agent (e.g., remdesivir or sofosbuvir) to the subject. In an embodiment, administering a combination of a hypericin compound and an antiviral agent to a subject results in a beneficial effect in the subject, e.g., compared with administering the hypericin compound and/or the antiviral agent (e.g., remdesivir or sofosbuvir) individually. For example, a combination of a hypericin compound and an antiviral agent may result in the reduced toxicity of the antiviral agent and/or an increase in efficacy of the antiviral agent in the subject.

In one aspect, the present disclosure features a method of treating a viral infection in a subject, comprising providing a combination of a hypericin compound and an antiviral agent to the subject wherein the molar amount of the hypericin compound in the combination is greater than the molar amount of the antiviral agent in the combination. In an embodiment, the efficacy of the combination is greater than the efficacy of the hypericin compound alone at the molar amount used in the combination. In an embodiment, the efficacy of the combination is greater than the efficacy of the antiviral agent alone at the molar amount used in the combination.

In an embodiment, each of the hypericin compound and the antiviral agent is independently formulated as a pharmaceutical composition. In an embodiment, the hypericin compound and the antiviral agent are formulated together as a pharmaceutical composition. In an embodiment, each of the hypericin compound and the antiviral agent is provided (e.g., administered) concomitantly to the subject. In an embodiment, each of the hypericin compound and the antiviral agent is provided (e.g., administered) sequentially to the subject. In an embodiment, the hypericin compound is provided (e.g., administered) to the subject prior to the antiviral agent. In an embodiment, the antiviral agent is provided (e.g., administered) to the subject prior to the hypericin compound. In an embodiment, the hypericin compound is selected from a compound listed in Table 1, or a pharmaceutically acceptable salt thereof In an embodiment, the antiviral agent is selected from remdesivir or sofosbuvir, or a pharmaceutically acceptable salt thereof.

DESCRIPTION

Figure 1:
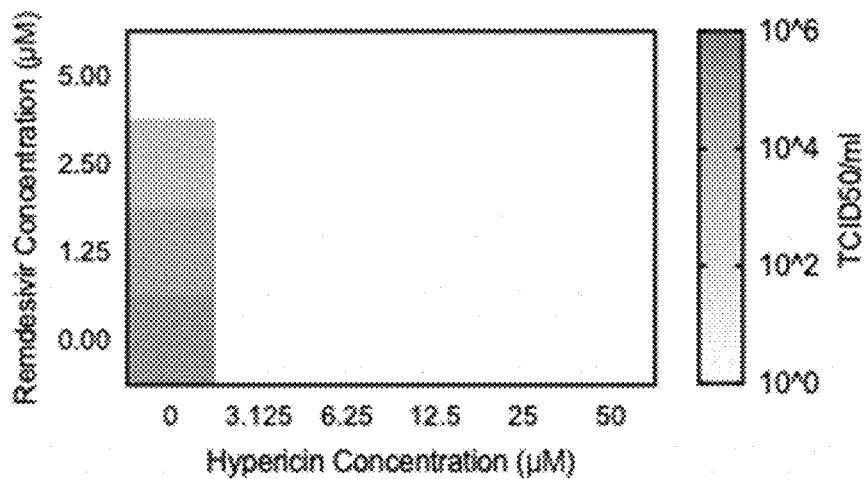
FIG. 1 is a graphic illustrating the reduction in viral titer in SARS-CoV-2 infected Vero E6 cells upon administration of hypericin and remdesivir.

Described herein are compositions comprising a hypericin compound (e.g., a compound of Formula (I) or a pharmaceutically acceptable salt thereof, e.g., hypericin or protohypericin) and antiviral agent (e.g., remdesivir), as well as methods of using the same to treat a viral infection in the subject, tissue, or cell. In an embodiment, administering a combination of a hypericin compound and an antiviral agent to a subject results in a beneficial effect in the subject, e.g., compared with administering the hypericin compound and/ or the antiviral agent individually. For example, a combination of a hypericin compound and an antiviral agent may result in the reduced toxicity of the antiviral agent and/or an increase in efficacy of the antiviral agent in the subject. A description of exemplary embodiments of the disclosure is provided herein.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the term "acquire" or "acquiring" as the terms are used herein, refer to obtaining possession of a physical entity (e.g., a sample, e.g., blood sample or liver biopsy specimen), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of a cell titer or a bodily fluid, e.g., via mass spectroscopy (e.g. LC-MS) or PCR (e.g., RT-PCR).

"Co-administration", "co-administering", "co-providing", "in combination" and "a combination of" as used herein in the context of the administration of a hypericin compound and an antiviral agent, refers to administration at the same time or administration of one therapy before (e.g., immediately before, less than about 5, about 10, about 15, about 30, about 45, about 60 minutes, about 1, about 2, about 3, about 4, about 6, about 8, about 10, about 12, about 16, about 20, about 24, about 48, about 72 or more hours before) administration of a secondary therapy. In some embodiments, the therapies to be co-administered are formulated in a single composition. In other embodiments, the therapies to be co-administered are formulated separately.

Numerous ranges, e.g., ranges for the amount of a therapy administered per day, are provided herein. In some embodiments, the range includes both endpoints. In other embodiments, the range excludes one or both endpoints. By way of example, the range can exclude the lower endpoint. Thus, in such an embodiment, a range of 250 to 400 mg/day, excluding the lower endpoint, would cover an amount greater than 250 that is less than or equal to 400 mg/day. The term "comprise" is intended to mean "include". Where a term is provided in the singular, it also contemplates aspects of the invention described by the plural of that term. The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

A "course" or "course of therapy," as referred to herein, comprises one or more separate administrations of a therapeutic agent or a combination of therapeutic agents (e.g., a hypericin compound (e.g., compound of Formula (I) or a pharmaceutically acceptable salt thereof) and/or an antiviral agent (e.g., remdesivir)). A course of therapy can comprise one or more cycles of a therapeutic agent. In some embodiments, a therapeutic agent is administered to a subject at least once, at least twice, at least three times, at least four times, or more over a course of treatment. A subject may be administered with one or more courses of treatment. In some embodiments, rest periods may be interposed between courses of treatment. For example, a rest period may be about 1, about 2, about 4, about 6, about 8, about 10, about 12, about 16, about 20, or about 24 hours; or about 1, about 2, about 3, about 4, about 5, about 6, or about 7 days; or about 1, about 2, about 3, about 4 or more weeks in length.

A "cycle", as used herein in the context of a cycle of administration of a therapeutic agent or a combination of therapeutic agents, refers to a period of time for which the therapeutic agent or combination of therapeutic agents is administered to a patient. For example, if a therapeutic agent is administered for a cycle of 4 weeks days, the periodic administration, e.g., daily or twice daily, is given for 4 weeks. A therapeutic agent or combination of therapeutic agents can be administered for more than one cycle. In some embodiments, the first and second or subsequent cycles are the same in terms of one or both of duration and periodic administration. In embodiments, a first and second or subsequent cycle differs in terms of one or both of duration and periodic administration. Rest periods may be interposed between cycles. A rest cycle may be about 1, about 2, about 4, about 6, about 8, about 10, about 12, about 16, about 20, or about 24 hours; or about 1, about 2, about 3, about 4, about 5, about 6, or about 7 days; or about 1, about 2, about 3, about 4 or more weeks in length.

The term "efficacy," as used herein in the context of a therapeutic agent or combination of therapeutic agents, refers to the ability of a therapeutic agent or a combination of therapeutic agents to effect a desirable treatment outcome, such as (i) the ability to decrease or inhibit viral infection-induced cytotoxicity; (ii) to decrease or inhibit viral replication or infection rate; (iii) to increase the viability of cells infected with, or at risk of infection by, a virus (e.g., a coronavirus, such as SARS-CoV coronavirus, MERS coronavirus, or SARS-CoV-2 coronavirus); (iv) to increase survival rate of a subject or patient infected with, or at risk of infection by, a virus (e.g., a coronavirus, such as SARS-CoV-2); (v) to decrease or alleviate one or more symptoms of viral infection (e.g., Covid-19 symptoms in a subject); or (vi) to inhibit one or more viral enzyme functions (e.g., one or more coronavirus helicases, coronavirus cysteine proteases, or coronavirus replicases).

As used herein, the terms "increasing" and "decreasing" refer to modulating that results in, respectively, greater or lesser amounts of function, expression, or activity of a particular metric relative to a reference. For example, subsequent to administration to a cell, tissue or subject of a combination of a hypericin compound and an antiviral agent described herein, the amount of a marker of a metric (e.g., cell viability, virulence) as described herein may be increased or decreased by at least 5%, 10%, 15%, 20%, 25%, 30%, 35%, 40%, 45%, 50%, 55%, 60%, 65%, 70; %, 75%, 80%, 85%, 90%, 95% or 98%, 2X, 3X, 5X, 10X or more relative to the amount of the marker prior to administration or relative to the effect of a negative control agent. The metric may be measured subsequent to administration at a time that the administration has had the recited effect, e.g., at least 12 hours, 24 hours, one week, one month, 3 months, or 6 months, after a treatment has begun.

As used herein, the terms "prevent" or "preventing" as used in the context of a disease or disorder described herein (e.g., a viral infection, e.g., a coronavirus infection), refer to administration of a hypericin compound in combination with an antiviral agent to a subject, e.g., the administration of a hypericin compound (e.g., compound of Formula (I) or a pharmaceutically acceptable salt thereof) and remdesivir, such that the onset of at least one symptom of the disorder or disease is delayed as compared to what would be seen in the absence of administration of said combination.

As used herein, the term "subject" is intended to include human and non-human animals. Exemplary human subjects include a human patient having a disease or disorder, e.g., a disorder described herein (e.g., a viral infection, e.g., a coronavirus infection), or a healthy subject. The term "non-human animals" includes all vertebrates, e.g., non-mammals (such as chickens, amphibians, reptiles) and mammals, such as non-human primates, domesticated and/or agriculturally useful animals, e.g., sheep, dogs, cats, cows, pigs, etc.

As used herein, an amount of a compound, conjugate, or substance effective to treat a disease or disorder (e.g., a viral infection described herein), "therapeutically effective amount," "effective amount" or "effective course" refers to an amount of the compound or composition which is effective, upon single or multiple dose administration(s) to a subject, in treating a subject, or in curing, alleviating, relieving or improving a subject with a disorder (e.g., a viral infection, e.g., a coronavirus infection) beyond that expected in the absence of such treatment.

As used herein, the terms "treat" or "treating" as used in the context of a disease or disorder described herein (e.g., a viral infection, e.g., a coronavirus infection), refer to administration of a hypericin compound in combination with an antiviral agent to a subject, e.g., the administration of a hypericin compound (e.g., compound of Formula (I)) and remdesivir, such that at least one symptom of the disorder or disease is cured, healed, alleviated, relieved, altered, remedied, ameliorated, or improved. Treating includes administering an amount effective to alleviate, relieve, alter, remedy, ameliorate, improve or affect the disorder or disease, or the symptoms of the disorder or disease. The treatment may inhibit deterioration or worsening of a symptom of a disorder or disease. In some embodiments, treating includes preventing. In some embodiments, treating does not include preventing.

Therapeutic Agents

Described herein are hypericin compounds administered in combination with an antiviral compound, e.g., remdesivir, to provide a therapeutic benefit to a cell or subject, e.g., treating a viral infection, reducing the toxicity of an antiviral agent, or decreasing the virulence of a viral infection in a subject.

Hypericin Compounds

As described herein, a hypericin compound comprises hypericin or an analog or variant thereof. Hypericin is a naphthodianthrone, a class of naturally occurring phenolic compounds comprising a 9,10-anthraquinone core structure. It is one of the principal active constituents of *Hypericum perforatium*, also known as Saint John's wort, a species of flowering plants often used in traditional medicine as an extract to treat numerous indications including depression.

In an embodiment, the hypericin compound is a compound of Formula (I):

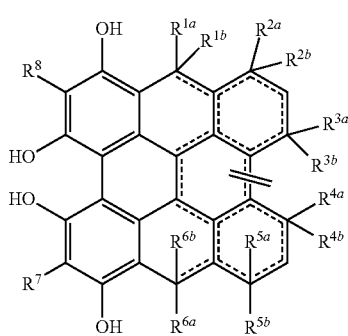

(I)

or a pharmaceutically acceptable salt thereof, wherein:

each of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^B R^C$, —$C(O)NR^B R^C$, —$NR^B C(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^9$; or $R^{1a}$ and $R^{1b}$, $R^{2a}$ and $R^{2b}$, $R^{3a}$ and $R^{3b}$, $R^{4a}$ and $R^{4b}$, $R^{5a}$ and $R^{5b}$, or $R^{6a}$ and $R^{6b}$ is independently taken together with the atoms to which they are attached to form an oxo group;

each of $R^7$ and $R^8$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^B R^C$, —$C(O)NR^B R^C$, —$NR^B C(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^{10}$;

each of $R^A$, $R^B$, $R^C$, and $R^D$ is hydrogen, $C_1$-$C_6$ alkyl, $C_1$-$C_6$ haloalkyl, $C_1$-$C_6$ heteroalkyl, cycloalkyl, or heterocyclyl;

each of $R^9$ and $R^{10}$ is independently $C_1$-$C_6$ alkyl, $C_1$-$C_6$ haloalkyl, $C_1$-$C_6$ heteroalkyl, halo, or cyano;

the bond indicated by "=" is either present or absent, wherein if the bond is absent, the corresponding carbon atoms are independently attached to hydrogen, $C_1$-$C_6$ alkyl, or halo; and each "═══" is independently a single or double bond, according to valency.

In an embodiment, $R^{1a}$ and $R^{1b}$ are taken together to form an oxo group. In an embodiment, $R^{2a}$ and $R^{2b}$ are taken together to form an oxo group. In an embodiment, $R^{5a}$ and $R^{5b}$ are taken together to form an oxo group. In an embodiment, $R^{6a}$ and $R^{6b}$ are taken together to form an oxo group. In an embodiment, each of $R^{1a}$ and $R^{1b}$ and $R^{6a}$ and $R^{6b}$ are taken together to form an oxo group.

In an embodiment, $R^{1a}$ and $R^{1b}$ are taken together to form an oxo group, and one of $R_{2a}$ and $R^{2b}$ is —$OR^A$ (e.g., —OH) and the other of $R^{2a}$ and $R^{2b}$ is hydrogen. In an embodiment, $R^{6a}$ and $R^{6b}$ are taken together to form an oxo group, and one of $R^{5a}$ and $R^{5b}$ is —$OR^A$ (e.g., —OH) and the other of $R^{5a}$ and $R^{5b}$ is hydrogen.

In an embodiment, $R^{3a}$ and $R^{3b}$ are each independently hydrogen, $C_1$-$C_6$ alkyl, $C_1$-$C_6$ haloalkyl, $C_1$-$C_6$ heteroalkyl, halo, cycloalkyl, or heterocyclyl. In an embodiment, $R^{3a}$ and $R^{3b}$ are each independently hydrogen, $C_1$-$C_6$ alkyl, or $C_1$-$C_6$ heteroalkyl. In an embodiment, one of $R^{3a}$ and $R^{3b}$ is hydrogen and the other of $R^{4a}$ and $R^{4b}$ is $C_1$-$C_6$ alkyl ($CH_3$) or $C_1$-$C_6$ heteroalkyl ($CH_2OH$).

In an embodiment, $R^{4a}$ and $R^{4b}$ are each independently hydrogen, $C_1$-$C_6$ alkyl, $C_1$-$C_6$ haloalkyl, $C_1$-$C_6$ heteroalkyl, halo, cycloalkyl, or heterocyclyl. In an embodiment, $R^{4a}$ and $R^{4b}$ are each independently hydrogen, $C_1$-$C_6$ alkyl, or $C_1$-$C_6$ heteroalkyl. In an embodiment, one of $R^{3a}$ and $R^{3b}$ is hydrogen and the other of $R^{4a}$ and $R^{4b}$ is $C_1$-$C_6$ alkyl ($CH_3$) or $C_1$-$C_6$ heteroalkyl ($CH_2OH$).

In an embodiment, $R^7$ is hydrogen, $C_1$-$C_6$ alkyl, $C_1$-$C_6$ haloalkyl, $C_1$-$C_6$ heteroalkyl, halo, cycloalkyl, or heterocyclyl. In an embodiment, $R^7$ is hydrogen. In an embodiment, $R^7$ is heterocyclyl. In an embodiment, $R^8$ is hydrogen, $C_1$-$C_6$ alkyl, $C_1$-$C_6$ haloalkyl, $C_1$-$C_6$ heteroalkyl, halo, cycloalkyl, or heterocyclyl. In an embodiment, $R^8$ is hydrogen. In an embodiment, $R^8$ is heterocyclyl.

In an embodiment, the hypericin compound is a compound of Formula (I-a):

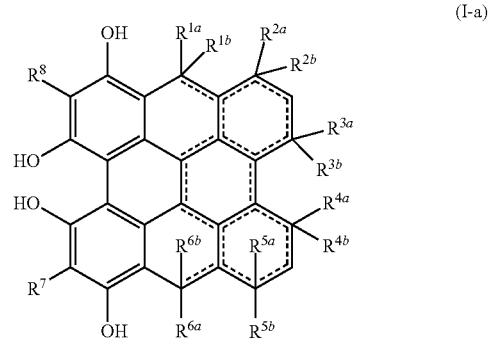

(I-a)

or a pharmaceutically acceptable salt thereof, wherein each of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^7$, $R^8$, and subvariables thereof are as defined for Formula (I).

In an embodiment, the hypericin compound is a compound of Formula (I-b):

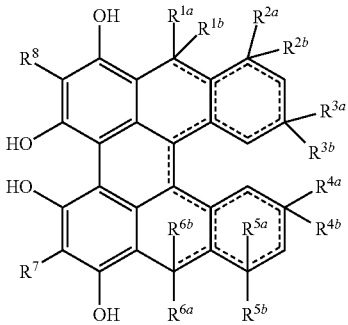

(I-b)

or a pharmaceutically acceptable salt thereof, wherein each of $R^{1a}$, $R^{1b}$, $R^{2a}$, $R^{2b}$, $R^{3a}$, $R^{3b}$, $R_{4a}$, $R^{4b}$, $R^{5a}$, $R^{5b}$, $R^{6a}$, $R^{6b}$, $R^7$, $R^8$, and subvariables thereof are as defined for Formula (I).

In an embodiment, the hypericin compound is a compound of Formula (I-c):

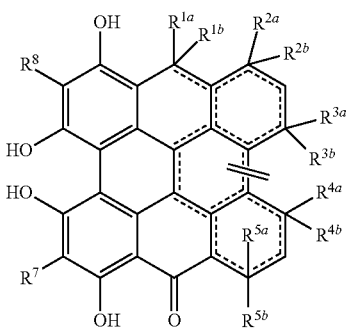

(I-c)

or a pharmaceutically acceptable salt thereof, wherein each of $R^{2a}$, $R^{2b}$, $R^{3a}$, $R^{3b}$, $R^{4a}$, $R^{4b}$, $R^{5a}$, $R^{5b}$, $R^7$, $R^8$, and subvariables thereof are as defined for Formula (I).

In an embodiment, the hypericin compound is a compound of Formula (I-d):

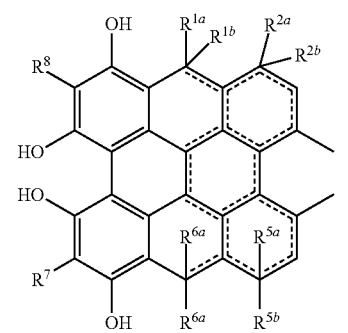

(I-d)

or a pharmaceutically acceptable salt thereof, wherein each of $R^{1a}$, $R^{1b}$, $R^{2a}$, $R^{2b}$, $R^{5a}$, $R^{5b}$, $R^{6a}$, $R^{6b}$, $R^7$, $R^8$, and subvariables thereof are as defined for Formula (I).

In an embodiment, the hypericin compound is a compound shown in Table 1.

TABLE 1

Exemplary hypericin compounds.

| Compound | Structure |
| --- | --- |
| Hypericin | 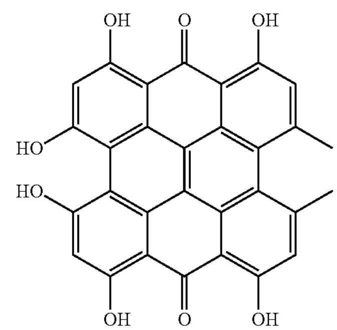 [SMILES: Cc1cc(O)c2c(=O)c3c(O)cc(O)c4c5c(O)cc(O)c6c(=O)c7c(O)cc(C)c8c1c2c(c34)c(c78)c65] |
| Protohypericin | 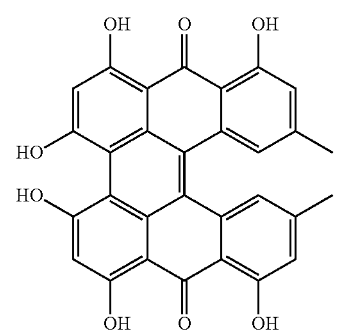 [SMILES: Cc1cc(O)c2c(=O)c3c(O)cc(O)c4c5c(O)cc(O)c6c(=O)c7c(O)cc(C)cc7c(c65)c(c2c1)c34] |
| Fagopyrine | 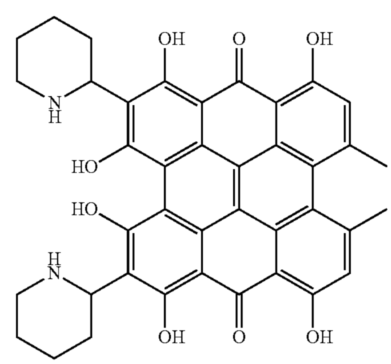 [SMILES: Cc1cc(O)c2c(=O)c3c(O)c(C4CCCCN4)c(O)c4c5c(O)c(C6CCCCN6)c(O)c6c(=O)c7c(O)cc(C)c8c1c2c(c34)c(c78)c65] |
| Pseudohypericin | 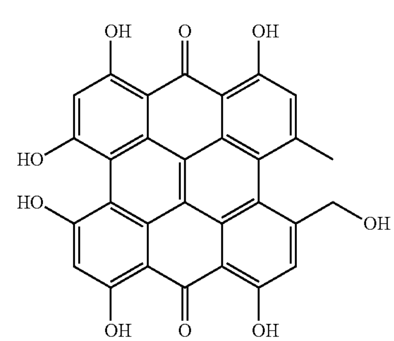 [SMILES: Cc1cc(O)c2c(=O)c3c(O)cc(O)c4c5c(O)cc(O)c6c(=O)c7c(O)cc(CO)c8c1c2c(c34)c(c65)c78] |

TABLE 1-continued

Exemplary hypericin compounds.

| Compound | Structure |
|---|---|
| Artonin A | 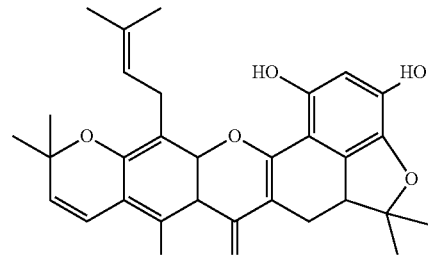 |
| Trisjuglone | 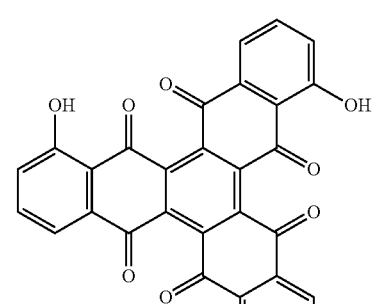 |

In an embodiment, the hypericin compound is hypericin or a pharmaceutically acceptable salt thereof In an embodiment, the hypericin compound is protohypericin or a pharmaceutically acceptable salt thereof. In an embodiment, the hypericin compound is fagopyrine or a pharmaceutically acceptable salt thereof. In an embodiment, the hypericin compound is pseudohypericin or a pharmaceutically acceptable salt thereof. In an embodiment, the hypericin compound is artonin A or a pharmaceutically acceptable salt thereof. In an embodiment, the hypericin compound is trisjuglone or a pharmaceutically acceptable salt thereof.

In an embodiment, the hypericin compound (e.g., hypericin) or a pharmaceutically acceptable salt thereof, is provided as a substantially pure compound, for example, at least 85%, at least 90%, at least 95%, at least 98%, at least 99%, or at least 99.9% pure, measured, e.g, by HPLC analysis. In embodiments described herein, the hypericin compound is provided as hypericin (CAS# 548-04-9) in the absence of hyperforin (CAS# 11079-53-1), adhyperforin (CAS# 143183-63-5), or other phloroglucinols that can naturally occur with hypericin in St. John's wort (*Hypericum perforatum*). In an embodiment, the hypericin compound is provided with less than 10%, 7.5%, 5%, 2.5%, 1%, 0.5%, or 0.1% hyperforin present. In an embodiment, the hypericin compound is provided with less than 10%, 7.5%, 5%, 2.5%, 1%, 0.5%, or 0.1% adhyperforin present.

A composition useful for the treatment of a viral infection (e.g., as described herein) may contain a single hypericin compound (e.g., hypericin) or a plurality of hypericin compounds. For example, a composition comprising a hypericin compound may contain only hypericin, e.g., synthetically prepared or extracted from a natural source. In contrast, a composition comprising a hypericin compound may also contain a combination of hypericin and a closely related analog or variant thereof, e.g., protohypericin or pseudohypericin.

The hypericin compounds provided herein may contain one or more asymmetric centers and thus occur as racemates and racemic mixtures, single enantiomers, individual diastereomers and diastereomeric mixtures. Further, the hypericin compounds may exist as one of many tautomeric forms. All such isomeric and tautomeric forms of these compounds are expressly included within the scope. Unless otherwise indicated when a compound is named or depicted by a structure without specifying the stereochemistry and has one or more chiral centers or tautomeric structures, it is understood to represent all possible stereoisomers or tautomers of the compound. The compounds provided herewith may also contain linkages (e.g., carbon-carbon bonds, phosphorus-oxygen bonds, or phosphorus-sulfur bonds) or substituents that can restrict bond rotation, e.g., restriction resulting from the presence of a ring or double bond.

Antiviral Agents

The present disclosure features administration of an antiviral agent to a subject or cell in combination with a hypericin compound (e.g., a hypericin compound described herein). In an embodiment, administration of the hypericin compound in combination with the antiviral agent results in an improvement of the therapeutic window for the antiviral agent, e.g., reducing toxicity of the antiviral agent or reducing the potency of the antiviral agent, e.g., in a subject or cell infected with a viral infection.

An antiviral agent for use in combination with a hypericin compound may be any antiviral agent known in the art. In an embodiment, the antiviral agent modulates (e.g., inhibits) a step in the viral life cycle, thus impairing the ability of the virus to replicate and/or propagate. For example, the antiviral agent may be an attachment inhibitor, post-attachment inhibitor, fusion inhibitor, entry inhibitor, uncoating inhibitor, protease inhibitor, polymerase inhibitor, nucleotide reverse transcriptase inhibitor, nucleoside reverse transcriptase inhibitor, non-nucleoside reverse transcriptase inhibitor, and integrase inhibitor. An attachment inhibitor may prevent recognition and/or attachment of a virus particle to a target cell. A post-attachment inhibitor may prevent engagement of the virus particle with the target cell at the site of attachment. A fusion inhibitor or entry inhibitor may prevent a virus particle from fusing with or otherwise entering a target cell. An uncoating inhibitor may prevent release of the contents of a viral particle into the target cell upon entry of the virus particle. Protease inhibitors, polymerase inhibitors, nucleotide reverse transcriptase inhibitors, nucleoside reverse transcriptase inhibitors, non-nucleoside reverse transcriptase inhibitors, and integrase inhibitors may prevent successful replication and/or packaging of viral genetic information in the target cell.

The antiviral agent may function by targeting a specific viral function, such as inhibiting a viral nucleic acid polymerase, viral protease, viral integrase, or viral neuraminidase. In another embodiment, the antiviral agent functions by targeting a host cell function required for successful viral replication, such as viral entry into a host cell, nucleic acid synthesis, protein synthesis, viral capsid assembly, or viral exit from the host cell.

In an embodiment, the antiviral agent is a capsid inhibitor, a secretion inhibitor, a microRNA, an anti sense RNA agent, an RNAi agent, or other agent designed to inhibit viral RNA. In an embodiment, the antiviral agent is a small molecule, a lipid, an oligonucleotide, a peptide, or an antibody. In an embodiment, the antiviral agent is a small molecule antiviral agent. The antiviral agent may be a nucleoside analog, a peptide, or a nonribosomal peptide.

In some embodiments, the antiviral agent targets a DNA virus. In some embodiments, the antiviral agent targets an RNA virus. In some embodiments, the antiviral agent has broad spectrum activity against numerous types of viruses, e.g., and is capable of targeting both a DNA virus and an RNA virus. Exemplary antiviral agents include abacavir, acyclovir, amantadine, ampligen, amprenavir, umifenovir, atripia, alazanavir, biktarvy, baloxavir marboxil, bulevirtide, boceprevir, chloroquine, cidofovir, cobicistat, combivir, daclatasvir, darunavir, delavirdine, descovy, didanosine, docosanol, dolutegravir, doravirine, edoxudine, efavirenz, elvitegravir, emtricitabine, enfuvirtide, entecavir, etravirine, ensitrelvir, famciclovir, favipirvir, fomivirsen, fosamprenavir, foscarnet, ganciclovir, hydroxychloroquine, ibacitabine, ibalizumab, idoxuridine, imiquimod, imunovir, ivermectin, indinavir, lamivudine, letermovir, lopinavir, loviride, maraviroc, methisazone, moroxydine, nelfinavir, nexavir, nitazoxanide, norvir, oseltamivir, penciclovir, peramvir, pleconaril, pieconaril, raltegravir, rilpivirine, ribavirin, remdesivir, ritonavir, saquinavir, sofosbuvir, taribavirin, telaprevir, tenofovir, telbivudine, trizivir, tipranavir, truvada, tromantadine, trifluridine, vidarabine, umifenovir, umifenovir, valaciclovir, vicriviroc, vidarabine, zalcitabine, zanamivir, and zicovidinr.

In an embodiment, the antiviral agent is a compound of Formula (II):

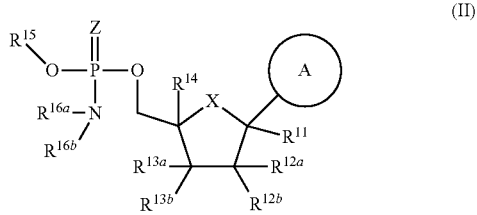

or a pharmaceutically acceptable salt thereof, wherein:

Ring A is a heteroaryl or heterocyclyl, each of which is optionally substituted with $R^{17}$ (e.g., a nucleobase or analog thereof);

X is O or NR';

Z is O or S;

each of $R^{11}$ and $R^{14}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, or cyano;

each of $R^{12a}$, $R^{12b}$, $R^{13a}$, and $R^{13b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, heterocyclyl, aryl, or heteroaryl, wherein each alkyl, alkenyl, alkynyl, haloalkyl, heteroalkyl, cycloalkyl, heterocyclyl, aryl, and heteroaryl is optionally substituted with one or more $R^{17}$; or $R^{15}$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, aryl, heteroaryl, cycloalkyl, or heterocyclyl, wherein each alkyl, cycloalkyl, and heterocyclyl is optionally substituted with one or more $R^{17}$;

each of $R^{16a}$ and $R^{16b}$ is independently hydrogen, $C_i$-$C_6$ alkyl, $C_2$-$C_6$ alkenyl, $C_2$-$C_6$ alkynyl, $C_1$-$C_6$ haloalkyl, $C_1$-$C_6$ heteroalkyl, —$C(O)R^D$, —$C_1$-$C_6$ alkylene-$C(O)O$-$C_1$-$C_6$ alkyl, —$C_1$-$C_6$ alkylene-$C(O)$-$C_1$-$C_6$ alkenyl, —$C_1$-$C_6$ alkylene-$C(O)O$-$C_1$-$C_6$ heteroalkyl, —$C_1$-$C_6$ alkylene-$C(O)$ $O$-$C_1$-$C_6$ haloalkyl, —$C_1$-$C_6$ alkylene-$C(O)O$-$C_1$-$C_6$ cycloalkyl, —$C_1$-$C_6$ alkylene-$C(O)O$-$C_1$-$C_6$ heterocyclyl, cycloalkyl, or heterocyclyl, wherein each alkyl, alkylene, alkenyl, alkynyl, haloalkyl, heteroalkyl, cycloalkyl, and heterocyclyl is optionally substituted with one or more $R^{18}$;

R' is hydrogen or $C_1$-$C_6$ alkyl;

each of $R^A$, $R^B$, $R^c$, and $R^D$ is hydrogen, $C_1$-$C_6$ alkyl, $C_1$-$C_6$ haloalkyl, $C_1$-$C_6$ heteroalkyl, cycloalkyl, or heterocyclyl; and each of $R^{17}$ and $R^{18}$ is independently $C_1$-$C_6$ alkyl, $C_1$-$C_6$ haloalkyl, $C_1$-$C_6$ heteroalkyl, halo, or cyano.

In an embodiment, the antiviral agent of Formula (II) is remdesivir. In an embodiment, the antiviral agent of Formula (II) is sofosbuvir.

In an embodiment, the antiviral agent is remdesivir or an analog thereof. The antiviral agent (e.g., remdesivir) may be isomerically pure or may be a mixture of various stereoisomers. For example, remdesivir may comprise the (R)-isomer, the (S)-isomer, or a mixture of both. In an embodiment, the antiviral agent is a remdesivir analog, e.g., as described in WO 2021/202907, which is incorporated herein by reference in its entirety.

Viral Infections

Described herein are methods for treating a viral infection in a subject, tissue, or cell. In embodiments, the cell is an isolated cell (e.g., a cell in a cell culture or a cell isolated from a tissue or intact organism). In embodiments, the cell is located in a tissue or organ. The viral infection occurs upon attachment and invasion of a host cell by a virion. Viruses are categorized into various classes, primarily based upon whether the virus is an RNA virus or a DNA virus. In an embodiment, the viral infection is an infection from an RNA virus (e.g., a positive-sense single-stranded RNA virus, a negative-sense single-stranded RNA virus, or a double-stranded RNA virus). In an embodiment, the viral infection is an infection from a DNA virus (e.g., a single-stranded DNA virus or a double-stranded DNA virus).

In an embodiment, the viral infection is caused by a double-stranded DNA virus. Exemplary double-stranded DNA viruses are in the *Adenoviridae, Herpesviridae, Papillomaviridae*, and *Poxviridae* viral families. For example, the virus may be an adenovirus, herpes simplex type 1 virus, herpes simplex virus type 2, varicella-zoster virus, Epstein-Barr virus, human cytomegalovirus, herpesvirus type 8, papillomavirus, BK virus, JC virus, or smallpox virus. In an embodiment, the viral infection is caused by a single-stranded DNA virus. Exemplary single-stranded DNA viruses are in the Parvoviridae viral family. For example, the virus may be a parvovirus B19 virus. In an embodiment, the viral infection is caused by a double-stranded RNA virus. Exemplary double-stranded RNA viruses are in the Reoviridae family. For example, the virus may be a rotavirus, orbivirus, coltivirus, or banna virus. In an embodiment, the viral infection is caused by a positive-sense single-stranded RNA virus. Exemplary positive-sense single-stranded RNA viruses are in the *Astroviridae, Caliciviridae, Coronaviridae, Flaviviridae, Hepeviridae, Matonaviridae*, or *Picornaviridae* viral families. For example, the virus may be a human astrovirus, Norwalk virus, human coronavirus 229E, human coronavirus NL63, human coronavirus OC43, human coronavirus HKU1, Middle East respiratory syndrome-related coronavirus, severe acute respiratory syndrome (SARS) coronavirus, severe acute respiratory syndrome (SARS) coronavirus 2, hepatitis C virus, yellow fever virus, Dengue virus, West Nile virus, TBE virus, Zika virus, hepatitis E, rubella virus, coxsackievirus, hepatitis A virus, poliovirus, or rhinovirus. In an embodiment, the viral infection is caused by a negative-sense single-stranded RNA virus. Exemplary negative-sense single-stranded RNA viruses are in the *Arenaviridae, Bunyaviridae, Filoviridae, Orthomyxoviridae, Paramyxoviridae, Pneumoviridae,* or *Rhabdoviridae* viral families. For example, the virus may be a Lassa virus, Crimean-Congo hemorrhagic fever virus, Hantaan virus, Ebola virus, Marburg virus, influenza virus, measles virus, mumps virus, parainfluenza virus, respiratory syncytial virus, rabies virus, hepatitis D virus. In an embodiment, the viral infection is caused by a single-stranded RNA retrovirus. Exemplary single-stranded RNA retroviruses are in the *Retroviridae* viral family. For example, the virus may be a human immunodeficiency virus. In an embodiment, the viral infection is caused by a double-stranded RNA retrovirus. Exemplary double-stranded RNA retroviruses are in the *Hepadnaviridae* viral family. For example, the virus may be a hepatitis B virus.

In an embodiment, the viral infection is caused by a coronavirus. Coronaviruses are a large family of viruses that are common in people and many different species of animals. Some coronaviruses can cause severe illness in people. Some notable coronaviruses include SARS coronavirus (SARS-CoV), which causes severe acute respiratory syndrome (SARS); MERS coronavirus (MERS-CoV), which causes Middle East respiratory syndrome (MERS); and SARS-CoV-2, which causes coronavirus disease 2019 (COVID-19). Infection with a coronavirus can cause fever, cough and shortness of breath. Infection can be particularly dangerous in older people, people with weakened immune systems, and people with underlying health conditions, such as cardiovascular disease, diabetes, and chronic lung disease, among others. In an embodiment, the viral infection is a SARS-CoV infection. In an embodiment, the viral infection is a MERS-CoV infection. In an embodiment, the viral infection is a SARS-CoV-2 infection.

Combination Therapies

Described herein are combination therapies comprising a hypericin compound and an antiviral agent (e.g., remdesivir) useful for the treatment of a viral infection. The combination therapy may be administered as a single formulation or as separate formulations. In an embodiment, the hypericin compound and the antiviral agent (e.g., remdesivir) are administered as a single pharmaceutical composition. In an embodiment, the hypericin compound and the antiviral agent (e.g., remdesivir) are administered as separate pharmaceutical compositions. In the case of separate formulations, the hypericin compound and the antiviral agent may be administered concomitantly or sequentially. In an embodiment, the hypericin compound and the antiviral agent (e.g., remdesivir) are administered concomitantly. In an embodiment, the hypericin compound and the antiviral agent (e.g., remdesivir) are administered sequentially. For example, the hypericin compound may be administered prior to the antiviral agent (e.g., remdesivir) or subsequent to the antiviral agent (e.g., remdesivir).

In some embodiments, the administration of the hypericin compound and the antiviral agent (e.g., remdesivir) has a synergistic or additive effect. For example, the administration of the hypericin compound and the antiviral agent (e.g., remdesivir) may have an additive effect, in which the therapeutic effect of the hypericin compound and the antiviral agent (e.g., remdesivir) is the total sum of the effects of each of the components individually. In contrast, the administration of the hypericin compound and the antiviral agent (e.g., remdesivir) may have a synergistic effect, in which the therapeutic effect of the hypericin compound and the antiviral agent (e.g., remdesivir) is greater than the sum of the individual components. The synergistic effect of the combination of the hypericin compound and the antiviral agent (e.g., remdesivir) may be 0.1%, 0.25%. 0.5%. 0.75%, 1%, 2%, 3%, 4%, 5%, 6%, 7%, 8%, 9%, 10%, 15%, 20%, 25%, 30%, 40%, 50%, 60%, 70%, 80%. 90%. 95%, or more than the total sum of the effects of the hypericin compound and the antiviral agent (e.g., remdesivir) administered individually. In an embodiment, the synergistic effect of the combination of the hypericin compound and the antiviral agent (e.g., remdesivir) is greater than between 5% and 75% of the total sum of the effects of the hypericin compound and the antiviral agent (e.g., remdesivir) administered individually.

In an embodiment, the synergistic effect of the combination of the hypericin compound and the antiviral agent (e.g., remdesivir) is greater than 10% of the total sum of the effects of the hypericin compound and the antiviral agent (e.g., remdesivir) administered individually. In an embodiment, the synergistic effect of the combination of the hypericin compound and the antiviral agent (e.g., remdesivir) is greater than 25% of the total sum of the effects of the hypericin compound and the antiviral agent (e.g., remdesivir) administered individually. In an embodiment, the synergistic effect of the combination of the hypericin compound and the antiviral agent (e.g., remdesivir) is greater than 50% of the total sum of the effects of the hypericin compound and the antiviral agent (e.g., remdesivir) administered individually. In an embodiment, the synergistic effect of the combination of the hypericin compound and the antiviral agent (e.g., remdesivir) is greater than 75% of the total sum of the effects of the hypericin compound and the antiviral agent (e.g., remdesivir) administered individually.

The synergistic effect of the combination of the hypericin compound and the antiviral agent (e.g., remdesivir) may be 1.5-fold, 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 75-fold, 100-fold, 200-fold, 500-fold greater or more than the total sum of the effects of the hypericin compound and the antiviral agent (e.g., remdesivir) administered individually. In an embodiment, the synergistic effect of the combination of the hypericin compound and the antiviral agent (e.g., remdesivir) is greater than between 2-fold and 100-fold of the total sum of the effects of the hypericin compound and the antiviral agent (e.g., remdesivir) administered individually. In an embodiment, the synergistic effect of the combination of the hypericin compound and the antiviral agent (e.g., remdesivir) is greater than between 5-fold and 50-fold of the total sum of the effects of the hypericin compound and the antiviral agent (e.g., remdesivir) administered individually. In one aspect, the amount of the hypericin compound and the amount of the antiviral agent are selected such that the molar concentration of the hypericin compound is greater than the molar concentration of the antiviral agent (e.g., remdesivir). For example, the molar concentration of the hypericin compound is greater than 1.5-fold, 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 75-fold, 100-fold, 200-fold, or 500-fold greater than the molar concentration of the antiviral agent (e.g., remdesivir). In an embodiment, the molar concentration of the hypericin compound is greater than 1.5-fold, 2-fold, 3-fold, 4-fold, 5-fold, 6-fold, 7-fold, 8-fold, 9-fold, or 10-fold greater than the molar concentration of the antiviral agent (e.g., remdesivir). In an embodiment, the molar concentration of the hypericin compound is between 2-fold and 20-fold greater than the molar concentration of the antiviral agent (e.g., remdesivir). In an embodiment, the molar concentration of the hypericin compound is between 5-fold and 10-fold greater than the molar concentration of the antiviral agent (e.g., remdesivir). In an embodiment, the molar concentration of the hypericin compound is about 5-fold greater than the molar concentration of the antiviral agent (e.g., remdesivir). In an embodiment, the molar concentration of the hypericin compound is about 10-fold greater than the molar concentration of the antiviral agent (e.g., remdesivir). In an embodiment, the molar concentration of the hypericin compound is about 15-fold greater than the molar concentration of the antiviral agent (e.g., remdesivir).

In another aspect, the combination of the hypericin compound with an antiviral agent (e.g., remdesivir) results in reducing the toxicity of the antiviral agent (e.g., remdesivir) in a subject or cell. For example, administration of a combination of the hypericin compound with an antiviral agent (e.g., remdesivir) may result in reducing the toxicity of the antiviral agent (e.g., remdesivir) in a subject or cell, compared with the toxicity of the antiviral agent (e.g., remdesivir) when administered to the subject or cell individually. In an embodiment, the toxicity of the antiviral agent (e.g., remdesivir) in a subject or cell is reduced upon administration of the antiviral agent (e.g., remdesivir) in combination with a hypericin compound, e.g., by about 0.1%, 0.25%. 0.5%. 0.75%, 1%, 2%, 3%, 4%, 5%, 6%, 7%, 8%, 9%, 10%, 15%, 20%, 25%, 30%, 40%, 50%, 60%, 70%, 80%. 90%. 95%, or more compared with the toxicity of the antiviral agent (e.g., remdesivir) when administered individually.

In another aspect, the combination of the hypericin compound with an antiviral agent (e.g., remdesivir) results in reducing the toxicity of the hypericin compound in a subject or cell.

For example, administration of a combination of the hypericin compound with an antiviral agent (e.g., remdesivir) may result in reducing the toxicity of the hypericin compound in a subject or cell, compared with the toxicity of the hypericin compound when administered to the subject or cell individually. In an embodiment, the toxicity of the hypericin compound in a subject or cell is reduced upon administration of an antiviral agent (e.g., remdesivir) in combination with a hypericin compound, e.g., by about 0.1%, 0.25%. 0.5%. 0.75%, 1%, 2%, 3%, 4%, 5%, 6%, 7%, 8%, 9%, 10%, 15%, 20%, 25%, 30%, 40%, 50%, 60%, 70%, 80%. 90%. 95%, or more compared with the toxicity of the hypericin compound when administered individually.

In an embodiment, the hypericin compound is administered at a dosage to provide a concentration of between 0.1 µM and 500 µM in a subject or cell. In an embodiment, the hypericin compound is administered at a dosage to provide a concentration of between 0.5 µM and 100 µM in a subject or cell. In an embodiment, the hypericin compound is administered at a dosage to provide a concentration of between 1µM and 100 µM in a subject or cell. In an embodiment, the hypericin compound is administered at a dosage to provide a concentration of between 1µM and 50 µM in a subject or cell. In an embodiment, the hypericin compound is administered at a dosage to provide a concentration of between 1 µM and 25 µM in a subject or cell. In an embodiment, the antiviral agent (e.g., remdesivir) is administered at a dosage to provide a concentration of between 0.01 µM and 50 µM in a subject or cell. In an embodiment, the antiviral agent (e.g., remdesivir) is administered at a dosage to provide a concentration of between 0.1 µM and 25 µM in a subject or cell. In an embodiment, the antiviral agent (e.g., remdesivir) is administered at a dosage to provide a concentration of between 0.1 µM and 10 µM in a subject or cell. In an embodiment, the antiviral agent (e.g., remdesivir) is administered at a dosage to provide a concentration of between 0.1 µM and 5 µM in a subject or cell.

In an embodiment, the antiviral agent (e.g., remdesivir) is administered at a dosage to provide a concentration of between 0.1 µM and 2.5 µM in a subject or cell.

In an embodiment, the hypericin compound is administered at a dosage to provide a concentration of between 0.1 µM and 500 µM and the antiviral agent (e.g., remdesivir) is administered at a dosage to provide a concentration of between 0.01 µM and 50 µM in a subject or cell. In an embodiment, the hypericin compound is administered at a dosage to provide a concentration of to provide a concentration of between 1 µM and 100 µM and the antiviral agent (e.g., remdesivir) is administered at a dosage to provide a concentration of between 0.1 µM and 25 µM in a subject or cell. In an embodiment, the hypericin compound is administered at a dosage to provide a concentration of to provide a concentration of between 1 µM and 25 µM and the antiviral agent (e.g., remdesivir) is administered at a dosage to provide a concentration of between 0.1 µM and 2.5 µM in a subject or cell.

In another aspect, the combination of the hypericin compound with an antiviral agent (e.g., remdesivir) results in reducing the virulence of a virus in a subject. Reducing the virulence may comprise one or more of (i) reducing the infection rate; (ii) reducing the doubling rate, e.g., amount of virus produced by an infected host cell; (iii) reducing the rate of viral DNA/RNA synthesis; (iv) reducing the rate of DNA/RNA mutations by a nucleic acid polymerase; and (v) reducing the rate of virion packaging. In an embodiment, reducing the virulence comprises (i). In an embodiment, reducing the virulence comprises (ii). In an embodiment, reducing the virulence comprises (iii). In an embodiment, reducing the virulence comprises (iv). In an embodiment, reducing the virulence comprises (v).

In an embodiment, the virulence of a virus is reduced in a subject by administering a combination of the hypericin compound with an antiviral agent (e.g., remdesivir). In an embodiment, the virulence of a virus is reduced in a subject or cell by about 0.1%, 0.25%. 0.5%. 0.75%, 1%, 2%, 3%, 4%, 5%, 6%, 7%, 8%, 9%, 10%, 15%, 20%, 25%, 30%, 40%, 50%, 60%, 70%, 80%. 90%. 95%, or more by administration of a combination of a hypericin compound and an antiviral agent (e.g., remdesivir) compared with administration of one of a hypericin compound or an antiviral agent individually.

Pharmaceutical Compositions

The present disclosure features methods for treating a subject infected with a viral infection, the methods comprising administering a hypericin compound (e.g., a compound of Formula (I) or in Table 1), an antiviral agent (e.g., a compound of Formula (II), e.g., remdesivir) or a combination thereof.

While it is possible for a hypericin compound (e.g., a compound of Formula (I) or in Table 1) or an antiviral agent (e.g., a compound of Formula (II), e.g., remdesivir) to be administered alone, it is preferable to administer said compound as a pharmaceutical composition or formulation, where the compounds are combined with one or more pharmaceutically acceptable diluents, excipients or carriers. The compounds according to the disclosure may be formulated for administration in any convenient way for use in human or veterinary medicine. In certain embodiments, the compounds included in the pharmaceutical preparation may be active itself, or may be a prodrug, e.g., capable of being converted to an active compound in a physiological setting. Regardless of the route of administration selected, the compounds of the present disclosure, which may be used in a suitable hydrated form, and/or the pharmaceutical compositions of the present disclosure, are formulated into a pharmaceutically acceptable dosage form such as described below or by other conventional methods known to those of skill in the art.

The amount and concentration of compounds of the present disclosure, e.g., a hypericin compound (e.g., a compound of Formula (I) or in Table 1) or an antiviral agent (e.g., a compound of Formula (II), e.g., remdesivir) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Thus, another aspect of the present disclosure provides pharmaceutically acceptable compositions comprising a therapeutically effective amount or prophylactically effective amount of a hypericin compound (e.g., a compound of Formula (I) or in Table 1) or an antiviral agent (e.g., a compound of Formula (II), e.g., remdesivir), formulated together with one or more pharmaceutically acceptable carriers (additives) and/or diluents. As described in detail below, the pharmaceutical compositions of the present disclosure may be specially formulated for administration in solid or liquid form, including those adapted for oral or parenteral administration, for example, by oral dosage, or by subcutaneous, intramuscular or intravenous injection as, for example, a sterile solution or suspension. However, in certain embodiments the subject compounds may be simply dissolved or suspended in sterile water. In certain embodiments, the pharmaceutical preparation is non-pyrogenic, i.e., does not elevate the body temperature of a patient.

The phrases "systemic administration," "administered systemically," "peripheral administration" and "administered peripherally" as used herein mean the administration of the compound other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, stabilizing agent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) ascorbic acid; (17) pyrogen-free water; (18) isotonic saline; (19) Ringer's solution; (20) ethyl alcohol; (21) phosphate buffer solutions; (22) cyclodextrins such as Captisol®; and (23) other non-toxic compatible substances such as antioxidants and antimicrobial agents employed in pharmaceutical formulations.

As set out above, certain embodiments of the compounds described herein may contain a basic functional group, such as an amine, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds of the present disclosure. These salts can be prepared in situ during the final isolation and purification of the compounds of the disclosure, or by separately reacting a purified compound of the disclosure in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

In other cases, the compounds of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the compound of the present disclosure (e.g of a hypericin compound (e.g., a compound of Formula (I) or in Table 1) or an antiviral agent (e.g., a compound of Formula (II), e.g., remdesivir)). These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. The pharmaceutically acceptable carriers, as well as wetting agents, emulsifiers, lubricants, coloring agents, release agents, coating agents, sweetening, flavoring agents, perfuming agents, preservatives, antioxidants, and other additional components may be present in an amount between about 0.001% and 99% of the composition described herein. For example, said pharmaceutically acceptable carriers, as well as wetting agents, emulsifiers, lubricants, coloring agents, release agents, coating agents, sweetening, flavoring agents, perfuming agents, preservatives, antioxidants, and other additional components may be present from about 0.005%, about 0.01%, about 0.05%, about 0.1%, about 0.25%, about 0.5%, about 0.75%, about 1%, about 1.5%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 85%, about 90%, about 95%, or about 99% of the composition described herein.

Pharmaceutical compositions of the present disclosure may be in a form suitable for oral administration, e.g., a liquid or solid oral dosage form. In some embodiments, the liquid dosage form comprises a suspension, a solution, a linctus, an emulsion, a drink, an elixir, or a syrup. In some embodiments, the solid dosage form comprises a capsule, tablet, powder, dragée, or powder. The pharmaceutical composition may be in unit dosage forms suitable for single administration of precise dosages. Pharmaceutical compositions may comprise, in addition to of a hypericin compound (e.g., a compound of Formula (I) or in Table 1) or an antiviral agent (e.g., a compound of Formula (II), e.g., remdesivir), a pharmaceutically acceptable carrier, and may optionally further comprise one or more pharmaceutically acceptable excipients, such as, for example, stabilizers (e.g., a binder, e.g., polymer, e.g., a precipitation inhibitor, diluents, binders, and lubricants.

In some embodiments, the composition described herein comprises a liquid dosage form for oral administration, e.g., a solution or suspension. In other embodiments, the composition described herein comprises a solid dosage form for oral administration capable of being directly compressed into a tablet. In addition, said tablet may include other medicinal or pharmaceutical agents, carriers, and or adjuvants. Exemplary pharmaceutical compositions include compressed tablets (e.g., directly compressed tablets), e.g., comprising one or more of a hypericin compound (e.g., a compound of Formula (I) or in Table 1) or an antiviral agent (e.g., a compound of Formula (II), e.g., remdesivir) or a pharmaceutically acceptable salt thereof.

Formulations of the present disclosure include those suitable for parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about 99 percent of active ingredient, preferably from about 5 percent to about 70 percent, most preferably from about 10 percent to about 30 percent. Pharmaceutical compositions of this disclosure suitable for parenteral administration comprise compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some embodiments, a compound of the present disclosure, such as a hypericin compound (e.g., a compound of Formula (I) or in Table 1), is provided as a composition in combination with an antiviral agent (e.g., a compound of Formula (II), e.g., remdesivir). For example, a hypericin compound (e.g., a compound of Formula (I) or in Table 1) may be prepared as a fixed dose composition in combination with or the antiviral agent (e.g., a compound of Formula (II), e.g., remdesivir). The fixed dose composition may be formulated for oral administration, e.g., as a solid dosage form or a liquid dosage form. In some embodiments, the liquid dosage form comprises a suspension, a solution, a linctus, an emulsion, a drink, an elixir, or a syrup. In some embodiments, the solid dosage form comprises a capsule, tablet, dragée, or powder.

The combination therapy described herein may involve formulation of the component agents for different routes of administration or for the same route of administration. For example, both the hypericin compound and the antiviral agent (e.g., remdesivir) may be formulated for oral administration. In another embodiment, the hypericin compound is formulated for oral administration and the antiviral agent (e.g., remdesivir) is formulated for parenteral administration. In another embodiment, the hypericin compound is formulated for parenteral administration and the antiviral agent (e.g., remdesivir) is formulated for oral administration. In an embodiment, the hypericin compound and the antiviral agent (e.g., remdesivir) are formulated as a fixed dose combination (e.g., as a liquid dosage form or solid dosage form, e.g., a capsule or tablet). In some embodiments, the hypericin compound and the antiviral agent (e.g., remdesivir) are formulated as a fixed dose combination (e.g., as a liquid dosage form or solid dosage form, e.g., a capsule or tablet) for oral administration.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin. In some cases, in order to prolong the effect of a compound of the present disclosure (e.g., a hypericin compound (e.g., a compound of Formula (I) or in Table 1) or an antiviral agent (e.g., a compound of Formula (II), e.g., remdesivir)) it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered form of the compound of the present disclosure is accomplished by dissolving or suspending compound in an oil vehicle.

In some embodiments, it may be advantageous to administer the hypericin compound (e.g., a compound of Formula (I) or in Table 1) or the antiviral agent (e.g., a compound of Formula (II), e.g., remdesivir) of the present disclosure in a sustained fashion. It will be appreciated that any formulation that provides a sustained absorption profile may be used. In certain embodiments, sustained absorption may be achieved by combining a compound of the present disclosure with other pharmaceutically acceptable ingredients, diluents, or carriers that slow its release properties into systemic circulation.

Routes of Administration

The hypericin compounds and antiviral agents, as well as other agents and related compositions thereof used in the methods described herein may be administered to a subject in a variety of forms depending on the selected route of administration, as will be understood by those skilled in the art. Exemplary routes of administration of the compositions used in the methods described herein include topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time.

In certain embodiments of the disclosure, the compositions described herein comprising a hypericin compound (e.g., a compound of Formula (I) or a compound of Table 1) are administered orally. In other embodiments of the disclosure, the compositions described herein comprising a hypericin compound (e.g., a compound of Formula (I) or a compound of Table 1) are administered intravenously. In certain embodiments of the disclosure, the compositions described herein comprising an antiviral agent (e.g., a compound of Formula (II), e.g., remdesivir) are administered orally. In other embodiments of the disclosure, the compositions described herein comprising an antiviral agent (e.g., a compound of Formula (II), e.g., remdesivir) are administered intravenously.

In an embodiment, the compositions described herein comprising a hypericin compound (e.g., a compound of Formula (I) or a compound of Table 1) is administered orally in combination with an antiviral agent (e.g., a compound of Formula (II), e.g., remdesivir). In an embodiment, the compositions described herein comprising a hypericin compound (e.g., a compound of Formula (I) or a compound of Table 1) is administered orally prior to or after oral administration of an antiviral agent (e.g., a compound of Formula (II), e.g., remdesivir). In other embodiments of the disclosure, the compositions described herein comprising a hypericin compound (e.g., a compound of Formula (I) or a compound of Table 1) is administered parenterally (e.g., intraperitoneally). In an embodiment, the compositions described herein comprising a hypericin compound (e.g., a compound of Formula (I) or a compound of Table 1) is administered parenterally in combination with an antiviral agent (e.g., a compound of Formula (II), e.g., remdesivir). In an embodiment, the compositions described herein comprising a hypericin compound (e.g., a compound of Formula (I) or a compound of Table 1) is administered parenterally prior to or after oral administration of an antiviral agent (e.g., a compound of Formula (II), e.g., remdesivir).

For intravenous, intraperitoneal, or intrathecal delivery or direct injection, the composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The choice of the route of administration will depend on whether a local or systemic effect is to be achieved. For example, for local effects, the composition can be formulated for topical administration and applied directly where its action is desired. For systemic, long-term effects, the composition can be formulated for enteral administration and given via the digestive tract. For systemic, immediate and/or short-term effects, the composition can be formulated for parenteral administration and given by routes other than through the digestive tract.

Dosages

The compositions of the hypericin compounds and antiviral agents as described herein may be formulated into acceptable dosage forms by conventional methods known to those of skill in the art. Actual dosage levels of the active ingredients in the compositions of the present disclosure (e.g., a hypericin compound or an antiviral agent) may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. A physician or veterinarian having ordinary skill in the art can readily determine and prescribe the effective amount of the composition required. For example, the physician or veterinarian can start doses of the hypericin compounds and/or antiviral agents of the disclosure employed in the composition at levels lower than that required in order to achieve the desired therapeutic effect and gradually increase the dosage until the desired effect is achieved. In general, a suitable daily dose of a composition of the present disclosure will be that amount of the substance which is the lowest dose effective to produce a therapeutic effect. Such an effective dose will generally depend upon the factors described herein. Preferably, the effective daily dose of a therapeutic composition may be administered as two, three, four, five, six or more sub-doses administered separately at appropriate intervals throughout the day, optionally, in unit dosage forms.

Preferred therapeutic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or via injection) to a subject afflicted with a disease or disorder described herein (e.g., a viral infection). Preferred prophylactic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or via injection) to a subject. The dose may also be titrated (e.g., the dose may be escalated gradually until signs of toxicity appear, such as headache, diarrhea, or nausea).

The frequency of treatment may also vary. The subject can be treated one or more times per day (e.g., once, twice, three, four or more times) or every so-many hours (e.g., about every 2, 4, 6, 8, 12, or 24 hours). The hypericin compound and/or antiviral agent concentration can be administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

In some embodiments, the dosage of a hypericin compound (e.g., a compound of Formula (I) or a compound of Table 1) is between about 5 mg/kg to about 100 mg/kg (e.g., about 5 mg/kg, about 10 mg/kg, about 15 mg/kg, about 20 mg/kg, about 30 mg/kg, about 40 mg/kg, about 50 mg/kg, about 60 mg/kg, about 70 mg/kg, about 80 mg/kg, about 90 mg/kg, or about 100 mg/kg). In some embodiments, the dosage of a hypericin compound (e.g., a compound of Formula (I) or a compound of Table 1) between about 10 mg/kg to about 50 mg/kg (e.g., about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg).

In some embodiments, the dosage of a hypericin compound (e.g., a compound of Formula (I) or a compound of Table 1) is about 0.1 mg to about 5 mg (e.g., about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.25 mg, about 1.5 mg, about 1.75 mg, about 2 mg, about 2.5 mg, about 3 mg, about 3.5 mg, about 4 mg, about 4.5 mg, or about 5 mg). In some embodiments, the dosage of a hypericin compound (e.g., a compound of Formula (I) or a compound of Table 1) is between about 0.01 mg/kg to about 10 mg/kg (e.g., about 0.01 mg/kg, about 0.025 mg/kg, about 0.05 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). In some embodiments, the dosage of a hypericin compound (e.g., a compound of Formula (I) or a compound of Table 1) is between about 0.1 mg/kg to about 5 mg/kg (e.g., about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.25 mg/kg, about 1.5 mg/kg, about 1.75 mg/kg, about 2 mg/kg, about 2.5 mg/kg, about 3 mg/kg, about 3.5 mg/kg, about 4 mg/kg, about 4.5 mg/kg, or about 5 mg/kg).

In some embodiments, a course of a hypericin compound (e.g., a compound of Formula (I) or a compound of Table 1) is between about 1 day to about 24 weeks. In some embodiments, the course of a hypericin compound (e.g., a compound of Formula (I) or a compound of Table 1) is administered at least weekly (e.g., once a week, twice a week, three times a week, four times a week, five times a week, six times a week, 7 times a week) throughout a course of treatment. In some embodiments, the course of a hypericin compound (e.g., a compound of Formula (I) or a compound of Table 1) is administered daily throughout a course of treatment.

In some embodiments, the dosage of an antiviral agent (e.g., a compound of Formula (II) e.g., remdesivir) is between about 5 mg/kg to about 100 mg/kg (e.g., about 5 mg/kg, about 10 mg/kg, about 15 mg/kg, about 20 mg/kg, about 30 mg/kg, about 40 mg/kg, about 50 mg/kg, about 60 mg/kg, about 70 mg/kg, about 80 mg/kg, about 90 mg/kg, or about 100 mg/kg). In some embodiments, the dosage of an antiviral agent (e.g., a compound of Formula (II) e.g., remdesivir) is between about 10 mg/kg to about 50 mg/kg (e.g., about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg).

In some embodiments, the dosage of an antiviral agent (e.g., a compound of Formula (II) e.g., remdesivir) is about 0.1 mg to about 5 mg (e.g., about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.25 mg, about 1.5 mg, about 1.75 mg, about 2 mg, about 2.5 mg, about 3 mg, about 3.5 mg, about 4 mg, about 4.5 mg, or about 5 mg). In some embodiments, the dosage of an antiviral agent (e.g., a compound of Formula (II) e.g., remdesivir) is between about 0.01 mg/kg to about 10 mg/kg (e.g., about 0.01 mg/kg, about 0.025 mg/kg, about 0.05 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). In some embodiments, the dosage of an antiviral agent (e.g., a compound of Formula (II) e.g., remdesivir) is between about 0.1 mg/kg to about 5 mg/kg (e.g., about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.25 mg/kg, about 1.5 mg/kg, about 1.75 mg/kg, about 2 mg/kg, about 2.5 mg/kg, about 3 mg/kg, about 3.5 mg/kg, about 4 mg/kg, about 4.5 mg/kg, or about 5 mg/kg).

In some embodiments, a course of an antiviral agent (e.g., a compound of Formula (II), e.g., remdesivir) is between about 1 day to about 24 weeks. In some embodiments, the course of antiviral agent (e.g., a compound of Formula (II), e.g., remdesivir) is administered at least weekly (e.g., once a week, twice a week, three times a week, four times a week, five times a week, six times a week, 7 times a week) throughout a course of treatment. In some embodiments, the course of an antiviral agent (e.g., a compound of Formula (II), e.g., remdesivir) is administered daily throughout a course of treatment.

Patient Selection and Monitoring

The methods of the present disclosure described herein entail administration of a combination of a hypericin compound and an antiviral agent (e.g., remdesivir) for the treatment of a viral infection (e.g., Covid-19). Accordingly, a patient and/or subject can be selected for treatment using a hypericin compound and an antiviral agent (e.g., remdesivir) for the treatment of a viral infection (e.g., Covid-19) by first evaluating the patient and/or subject to determine whether the subject is infected with a viral infection (e.g., Covid-19) and determination of the serotypic and genotypic classification of the virus. A subject can be evaluated as infected with a viral infection using methods known in the art. The subject can also be monitored, for example, subsequent to administration of a compound described herein (e.g., a hypericin compound and an antiviral agent (e.g., remdesivir)) or a pharmaceutically acceptable salt thereof.

In some embodiments, the subject is a mammal. In some embodiments, the subject is a human. In some embodiments, the subject is an adult. In some embodiments, the subject has an acute form of a viral infection. In some embodiments, the subject has a chronic form of a viral infection. In some embodiments, the subject has been diagnosed with a viral infection.

In some embodiments, the subject has a coronavirus infection (SARS-CoV-2 infection), e.g., Covid-19. In some embodiment, the subject has been diagnosed with a coronavirus infection, e.g., Covid-19. In some embodiments, the subject has Covid-19 and the classification of the Covid-19 infection is known. Exemplary classes of SARS-CoV-2 viral infections include alpha (B.1.1.7 or Q lineage), beta (B.1.351 or a descendant lineage), gamma (P.1 or a descendant lineage), delta (B.1.617.2 or AY lineage), epsilon (B.1.427 or B.1.429 lineage), eta (B.1.525 lineage), iota (B.1.526 lineage), kappa (B.1.617.1 lineage), 1.617.3, mu (B.1.621 or B.1.621.1 lineage), omicron (B.1.1.529, BA.1, BA.1.1, BA.2, BA.3, BA.4, or BA.5 lineage) and zeta (P.2 lineage). In some embodiments, the subject is infected with SARS CoV-2 alpha (B.1.1.7 or Q lineage). In some embodiments, the subject is infected with SARS CoV-2 beta (B.1.351 or a descendant lineage). In some embodiments, the subject is infected with SARS CoV-2 gamma (P.1 or a descendant lineage). In some embodiments, the subject is infected with SARS CoV-2 delta (B.1.617.2 or AY lineage). In some embodiments, the subject is infected with SARS CoV-2 epsilon (B.1.427 or B.1.429 lineage). In some embodiments, the subject is infected with SARS CoV-2 eta (B.1.525 lineage). In some embodiments, the subject is infected with SARS CoV-2 iota (B.1.526 lineage). In some embodiments, the subject is infected with SARS CoV-2 kappa (B.1.617.1 lineage). In some embodiments, the subject is infected with SARS CoV-2 mu (B.1.621 or B.1.621.1 lineage). In some embodiments, the subject is infected with SARS CoV-2 omicon (B.1.1.529, BA.1, BA.1.1, BA.2, BA.3, BA.4, or BA.5 lineage). In some embodiments, the subject is infected with SARS CoV-2 zeta (P.2 lineage).

In some embodiments, the subject is treatment naïve. In some embodiments, the subject has previously been treated for a coronavirus (e.g., SARS CoV-2) infection. For example, the subject may have received a vaccine or other coronavirus therapy. In some embodiments, the subject is suffering from a relapsed coronavirus (e.g., SARS CoV-2) infection. In some embodiments, the subject has been treated with an anti-coronavirus (e.g., SARS CoV-2) agent other than a hypericin compound or antiviral agent (e.g., remdesivir) described herein and is suffering from a relapsed coronavirus (e.g., SARS CoV-2) infection. In some embodiments, the subject has been treated with a nucleoside analog, a non-nucleoside antiviral, or an immune enhancer and is suffering from a relapsed coronavirus (e.g., SARS CoV-2) infection. In some embodiments, the subject has been treated with a nucleoside analog, e.g., lamivudine, adefovir dipivoxil, entecavir, telbivudine, clevudine, ribavarin, tenofovir, tenofovir alafenamide, besifovir, or AGX-1009, and is suffering from a relapsed coronavirus (e.g., SARS CoV-2) infection. In some embodiments, the subject has been treated with a non-nucleoside antiviral agent, e.g., NOV-225, BAM 205, Myrcludex B, ARC-520, BAY 41-4109, REP 9AC, Alinia (nitazoxanide), Dd-RNAi, NVR-121 (NVR 3-778), BSBI-25, or NVP-018, and is suffering from a relapsed viral infection. In some embodiments, the subject has been treated with an immune enhancer, e.g., zadaxin (thymosin alpha-1), GS-4774, CYT107 (interleukin-7), or Dv-601, and is suffering from a relapsed viral infection.

In some embodiments, the subject has a co-morbidity, such as heart disease, coronary artery disease, a cardiomyopathy, diabetes, obesity, high blood pressure, cancer, cerebrovascular disease, chronic kidney disease, chronic liver disease, cystic fibrosis, an immunodeficiency, and tuberculosis. In some embodiments, the subject has been diagnosed with diabetes (e.g., type 1 diabetes or type 2 diabetes). In some embodiments, the subject has been diagnosed with heart disease, coronary artery disease, a cardiomyopathy, or high blood pressure. In some embodiments, the subject is a smoker. In some embodiments, the subject has a body mass index (BMI) greater than about 30 kg/m$^2$.

In some embodiments, the methods described herein further comprise analyzing or receiving analysis of a sample from the subject at least once prior to the end of treatment. In some embodiments, the blood sample is analyzed for viral load and viral antigen levels. In some embodiments, the blood sample is analyzed for the expression level of a cytokine. In some embodiments, the blood sample is analyzed for the presence of anti-SARS-CoV-2 antibodies.

In some embodiments, the methods described herein further comprise analyzing or receiving analysis of a biopsy specimen from the subject at least once prior to the end of treatment. In some embodiments, the biopsy specimen is analyzed for the levels of viral DNA, viral RNA, and/or viral antigens.

Additional Agents

In some embodiments, additional therapeutic agents may be administered with compositions of the present disclosure for the treatment of a viral infection, such as a coronavirus infection (e.g., Covid-19), or any symptom or associated condition thereof. When combination therapy is employed, the additional therapeutic agent(s) can be administered as a separate formulation or may be combined with any of the compositions described herein.

For example, any of the methods described herein may further comprise the administration of a therapeutically effective amount of an additional agent in conjunction with a a hypericin compound or an antiviral agent (e.g., remdesivir). Exemplary additional agents include an immune therapy, a vaccine, an anti-inflammatory agent, a pain reliever, a mucolytic agent, a cancer therapy, an antiviral agent, an antifungal agent, an antibacterial agent, a bronchodilator, or a vasodilator.

In some embodiments, the additional agent is an anti-inflammatory agent. For example, the anti-inflammatory agent may be an angiotensin-converting enzyme 2 (ACE-2) inhibitor (e.g., lisinopril, benazepril, captopril, enalapril, fosinopril, moexipril, perindopril, or quinapril), a corticosteroid (e.g., cortisone, prednisone, prednisolone, methylprednisolone, dexamethasone, betamethasone, or hydrocortisone) or a non-steroidal anti-inflammatory drug (NSAID) (e.g., ibuprofen, naproxen, diclofenac, celecoxib, mefenamic acid, etoricoxib, or indomethacin).

In some embodiments, the additional agent is a cancer therapy. In some embodiments, the cancer therapy agent is selected from methotrexate, 5-fluorouracil, doxorubicin, vincristine, bleomycin, vinblastine, dacarbazine, toposide, cisplatin, epirubicin, and sorafenib tosylate.

In some embodiments, the additional agent is a second antiviral agent. In some embodiments, the antiviral agent comprises an interferon, a nucleoside analog, a non-nucleoside antiviral, or a non-interferon immune enhancer. In some embodiments, the additional antiviral agent comprises penciclovir, peramivir, oseltamivir, lamivudine, adefovir dipivoxil, entecavir, telbivudine, clevudine, ribavarin, tenofovir, besifovir, AGX-1009, NOV-225, BAM 205, Myrcludex B, ARC-520, BAY 41-4109, REP 9AC, Alinia (nitazoxanide), Dd-RNAi, NVR-121 (NVR 3-778), BSBI-25, NVP-018, zadaxin (thymosin alpha-1 ), GS-4774, CYT107 (interleukin-7), Dv-601, or GS-9620.

Administration in combination can proceed by any technique apparent to those of skill in the art including, for example, separate, sequential, concurrent, and alternating administration.

ENUMERATED EMBODIMENTS

1. A method of treating a viral infection in a subject, comprising providing a combination of a hypericin compound and an antiviral agent to the subject,
wherein the molar amount of the hypericin compound in the combination is greater than the molar amount of the antiviral agent,
thereby treating the viral infection in the subject.
2. The method of embodiment 1, wherein the efficacy of the combination is greater than:
(i) the efficacy of the hypericin compound alone at the molar amount used in the combination; or
(ii) the efficacy of the antiviral agent alone at the molar amount used in the combination.
3. The method of any one of embodiments 1-2, comprising (i).
4. The method of any one of embodiments 1-3, comprising (ii).
5. The method of any one of the preceding embodiments, wherein the efficacy of the combination is at least $X_1$-fold greater than the efficacy of the hypericin compound alone at the molar amount used in the combination, wherein $X_1$ is 1, 1.25, 1.5, 1.75, 2, 2.5, or greater.
6. The method of any one of the preceding embodiments, wherein the efficacy of the combination is at least $X_1$-fold greater than the efficacy of the antiviral agent alone at the molar amount used in the combination, wherein $X_1$ is 1, 1.25, 1.5, 1.75, 2, 2.5, or greater.
7. The method of any one of the preceding embodiments, wherein providing the combination comprises administering the combination to the subject.
8. The method of any one of the preceding embodiments, wherein the molar amount of the hypericin compound in the combination comprises the molar concentration of the hypericin compound in the combination.
9. The method of any one of the preceding embodiments, wherein the molar amount of the antiviral agent in the combination comprises the molar concentration of the antiviral agent in the combination.
10. The method of any one of the preceding embodiments, wherein each of the hypericin compound and the antiviral agent is independently formulated as a pharmaceutical composition.
11. The method of any one of the preceding embodiments, wherein the hypericin compound and the antiviral agent are formulated together as a pharmaceutical composition.
12. The method of any one of the preceding embodiments, wherein each of the hypericin compound and the antiviral agent is provided (e.g., administered) concomitantly to the subject.
13. The method of any one of embodiments 1-11, wherein each of the hypericin compound and the antiviral agent is provided (e.g., administered) sequentially to the subject.
14. The method of embodiment 13, wherein the hypericin compound is provided (e.g., administered) to the subject prior to the antiviral agent.
15. The method of embodiment 13, wherein the antiviral agent is provided (e.g., administered) to the subject prior to the hypericin compound.
16. The method of any one of the preceding embodiments, wherein the hypericin compound is a compound of Formula (I):

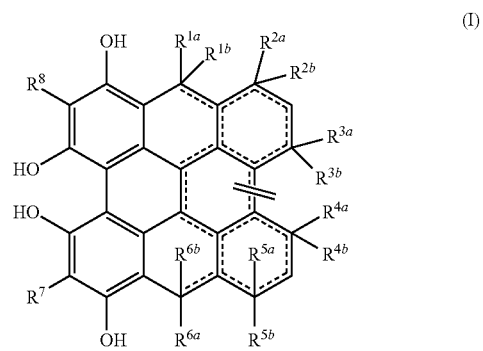

or a pharmaceutically acceptable salt thereof, wherein:
each of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^9$; or
$R^{1a}$ and $R^{2b}$, $R^{2a}$ and $R^{2b}$, $R^{3a}$ and $R^{3b}$, $R^{4a}$ and $R^{4b}$, $R^{5a}$ and $R^{5b}$, or $R^{6a}$ and $R^{6b}$ is independently taken together with the atoms to which they are attached to form an oxo group;

each of $R^7$ and $R^8$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^{10}$;

each of $R^A$, $R^B$, $R^C$, and $R^D$ is hydrogen, $C_1$-$C_6$ alkyl, $C_1$-$C_6$ haloalkyl, $C_1$-$C_6$ heteroalkyl, cycloalkyl, or heterocyclyl;

each of $R^9$ and $R^{10}$ is independently $C_1$-$C_6$ alkyl, $C_1$-$C_6$ haloalkyl, $C_1$-$C_6$ heteroalkyl, halo, or cyano;

the bond indicated by "=" is either present or absent, wherein if the bond is absent, the corresponding carbon atoms are independently attached to hydrogen, $C_1$-$C_6$ alkyl, or halo; and each "═══" is independently a single or double bond, according to valency.

17. The method of embodiment 16, wherein $R^{1a}$ and $R^{1b}$ are taken together to form an oxo group.

18. The method of any one of embodiments 16-17, wherein one of $R^{2a}$ and $R^{2b}$ is —$OR^A$ (e.g., —OH) and the other of $R^{2a}$ and $R^{2b}$ is hydrogen.

19. The method of any one of embodiments 16-18, wherein $R^{6a}$ and $R^{6b}$ are taken together to form an oxo group.

20. The method of any one of embodiments 16-19, wherein one of $R^{5a}$ and $R^{5b}$ is —$OR^A$ (e.g., —OH) and the other of $R^{5a}$ and $R^{5b}$ is hydrogen.

21. The method of any one of the preceding embodiments, wherein the hypericin compound is prepared synthetically or is extracted from a natural source (e.g., St. John's Wort).

22. The method of embodiment 21, wherein the hypericin compound is prepared synthetically.

23. The method of embodiment 22, wherein the hypericin compound is extracted from a natural source (e.g., St. John's Wort).

24. The method of any one of the preceding embodiments, wherein the hypericin compound is a compound selected from Table 1 or a pharmaceutically acceptable salt thereof.

25. The method of embodiment 24, wherein the hypericin compound is substantially pure.

26. The method of any one of embodiments 24-25, wherein the hypericin compound is provided as a pharmaceutical composition and the pharmaceutical composition comprises less than about 50%, 55%, 60%, 65%, 70%, 75%, 80%, 85%, 90%, 95%, 99%, or 99.9% of another compound.

27. The method of any one of embodiments 24-26, wherein the hypericin compound is provided as a pharmaceutical composition and the pharmaceutical composition comprises less than about 50%, 55%, 60%, 65%, 70%, 75%, 80%, 85%, 90%, 95%, 99%, or 99.9% of another compound listed in Table 1 or a pharmaceutically acceptable salt thereof.

28. The method of any one of embodiments 24-27, wherein the hypericin compound is provided as a pharmaceutical composition and the pharmaceutical composition comprises less than about 50%, 55%, 60%, 65%, 70%, 75%, 80%, 85%, 90%, 95%, 99%, or 99.9% of a compound present in St. John's Wort.

29. The method of any one of the preceding embodiments, wherein the hypericin compound is provided in the combination in the absence of hyperforin, adhyperforin, or a pharmaceutically acceptable salt thereof.

30. The method of any one of the preceding embodiments, wherein the hypericin compound is hypericin or a pharmaceutically acceptable salt thereof.

31. The method of embodiment 30, wherein the hypericin or a pharmaceutically acceptable salt thereof is provided in the combination in the absence of hyperforin, adhyperforin, or a pharmaceutically acceptable salt thereof 32. The method of any one of embodiments 30-31, wherein the hypericin or a pharmaceutically acceptable salt thereof is provided as a pharmaceutical composition, and the pharmaceutical composition comprises less than about 90%, 95%, 99%, or 99.9% of another compound in listed in Table 1 or a pharmaceutically acceptable salt thereof.

33. The method of any one of the preceding embodiments, wherein the antiviral agent comprises a small molecule, antibody, peptide, or oligonucleotide.

34. The method of any one of the preceding embodiments, wherein the antiviral agent is an agent that modulates a step in the viral life cycle.

35. The method of any one of the preceding embodiments, wherein the antiviral agent is selected from the group consisting of an attachment inhibitor, post-attachment inhibitor, fusion inhibitor, entry inhibitor, uncoating inhibitor, protease inhibitor, polymerase inhibitor, nucleotide reverse transcriptase inhibitor, nucleoside reverse transcriptase inhibitor, non-nucleoside reverse transcriptase inhibitor, and integrase inhibitor.

36. The method of any one of the preceding embodiments, wherein the antiviral agent comprises a nucleoside analog or a non-ribosomal peptide.

37. The method of any one of the preceding embodiments, wherein the antiviral agent is compound of Formula (II):

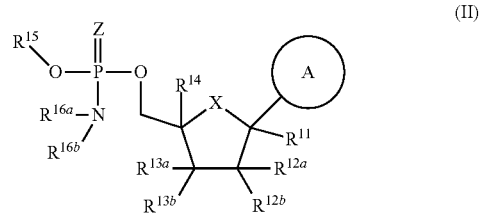

(II)

or a pharmaceutically acceptable salt thereof, wherein:

Ring A is a heteroaryl or heterocyclyl, each of which is optionally substituted with $R^{17}$ (e.g., a nucleobase or analog thereof);

X is O or $NR'$;

Z is O or S;

each of $R^{11}$ and $R^{14}$ is independently hydrogen, $C_1$-$C_6$ alkyl, $C_1$-$C_6$ alkenyl, $C_1$-$C_6$ alkynyl, $C_1$-$C_6$ haloalkyl, $C_1$-$C_6$ heteroalkyl, halo, or cyano;

each of $R^{12a}$, $R^{12b}$, $R^{13a}$, and $R^{13b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, heterocyclyl, aryl, or heteroaryl, wherein each alkyl, alkenyl, alkynyl, haloalkyl, heteroalkyl, cycloalkyl, heterocyclyl, aryl, and heteroaryl is optionally substituted with one or more $R^{17}$; or $R^{15}$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, aryl, heteroaryl, cycloalkyl, or heterocyclyl, wherein each alkyl, cycloalkyl, and heterocyclyl is optionally substituted with one or more $R^{17}$;

each of $R^{16a}$ and $R^{16b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, —(O)$R^D$, —$C_1$-$C_6$ alkylene-C(O)O-$C_1$-$C_6$ alkyl, —$C_1$-$C_6$ alkylene-C(O)-$C_1$-$C_6$ alkenyl, —$C_1$-$C_6$ alkylene-C(O)O-$C_1$-$C_6$ heteroalkyl, —$C_1$-$C_6$ alkylene-C(O)O-$C_1$-$C_6$ haloalkyl, —$C_1$-$C_6$ alkylene-C(O)O-$C_1$-$C_6$ cycloalkyl, —$C_1$-$C_6$ alkylene-C(O)O-$C_1$-$C_6$ heterocyclyl, cycloalkyl, or heterocyclyl, wherein each alkyl, alkylene, alkenyl, alkynyl, haloalkyl, heteroalkyl, cycloalkyl, and heterocyclyl is optionally substituted with one or more $R^{18}$;

R' is hydrogen or $C_1$-$C_6$ alkyl;

each of $R^A$, $R^B$, $R^C$, and $R^D$ is hydrogen, $C_1$-$C_6$ alkyl, $C_1$-$C_6$ haloalkyl, $C_1$-$C_6$ heteroalkyl, cycloalkyl, or heterocyclyl; and each of $R^{17}$ and $R^{18}$ is independently $C_1$-$C_6$ alkyl, $C_1$-$C_6$ haloalkyl, $C_1$-$C_6$ heteroalkyl, halo, or cyano.

38. The method of any one of the preceding embodiments, wherein the antiviral agent targets an RNA virus.

39. The method of any one of the preceding embodiments, wherein the antiviral agent is selected from remdesivir, sofosbuvir, or a pharmaceutically acceptable salt thereof.

40. The method of any one of the preceding embodiments, wherein the antiviral agent is selected from remdesivir or a pharmaceutically acceptable salt thereof 41. The method of any one of the preceding embodiments, wherein the hypericin compound is administered at a dosage to provide a concentration of between 0.1 µM and 500 µM in the subject or a cell.

42. The method of any one of the preceding embodiments, wherein the hypericin compound is administered at a dosage to provide a concentration of between 1 µM and 25 µM in the subject or a cell.

43. The method of any one of the preceding embodiments, wherein the antiviral agent (e.g., remdesivir) is administered at a dosage to provide a concentration of between 0.01 µM and 25 µM in the subject or a cell.

44. The method of any one of the preceding embodiments, wherein the antiviral agent (e.g., remdesivir) is administered at a dosage to provide a concentration of between 0.1 µM and 5 µM in the subject or a cell.

45. The method of any one of the preceding embodiments, wherein the ratio of the amount of hypericin compound to the antiviral agent in the combination is between 200:1 to 1:1.

46. The method of embodiment 45, wherein the ratio of the amount of hypericin compound to the antiviral agent in the combination is between 50:1 to 1:1.

47. The method of any one of embodiments 45-46, wherein the ratio of the amount of hypericin compound to the antiviral agent in the combination is between 50:1 to 2:1.

48. The method of any one of embodiments 45-47, wherein the ratio of the amount of hypericin compound to the antiviral agent in the combination is between 25:1 to 2:1.

49. The method of any one of the preceding embodiments, wherein:

(i) the hypericin compound is hypericin or a pharmaceutically acceptable salt thereof;

(ii) the antiviral agent is remdesivir or a pharmaceutically acceptable salt thereof; and (iii) the molar amount of the hypericin compound in the combination is between 20-fold and 5-fold greater than the molar amount of the antiviral agent (e.g., remdesivir).

50. The method of any one of the preceding embodiments, further comprising administration of an additional agent.

51. The method of any one of the preceding embodiments, wherein the subject is a mammal (e.g., a human).

52. The method of any one of the preceding embodiments, wherein the viral infection is present within a virally infected organ, tissue, or cell in a subject.

53. The method of embodiment 52, wherein the virally infected organ is selected from the group consisting of the brain, spinal cord, eye, skin, lung, heart, pancreas, large intestine, small intestine, stomach, liver, gall bladder, kidney, or spleen.

54. The method of embodiment 52, wherein the virally infected tissue is selected from the group consisting of lung tissue, tracheal tissue, intestinal tissue, skin tissue, pancreatic tissue, vascular tissue, mucosal tissue, kidney tissue, brain tissue, nervous tissue, or cardiac tissue.

55. The method of embodiment 52, wherein the virally infected cell comprises an angiotensin-converting enzyme 2 (ACE2) receptor on the cell surface.

56. The method of embodiment 52, wherein the virally infected cell is selected from the group consisting of an epithelial cell or an endothelial cell.

57. The method of embodiment 52, wherein the virally infected cell is a basal cell, luminal cell, secretory cell, or ciliated cell.

58. The method of any one of embodiments 52-57, wherein the virally infected cell is a bronchial cell, renal cell, enterocyte, goblet cell, skin cell, islet cell, neuronal cell, glial cell, or heart cell.

59. The method of any one of the preceding embodiments, wherein the viral infection is a coronavirus infection.

60. The method of any one of the preceding embodiments, wherein the viral infection is a SARS coronavirus (SARS-CoV) infection, MERS coronavirus (MERS-CoV) infection, or SARS-CoV-2 infection.

61. The method of any one of the preceding embodiments, wherein the viral infection is a SARS CoV-2 infection.

62. A method of treating a SARS CoV-2 infection in a cell or a subject, comprising providing a combination of (i) hypericin or a pharmaceutically acceptable salt thereof and (ii) remdesivir or a pharmaceutically acceptable salt thereof to the cell or subject, wherein of the molar ratio of hypericin to remdesivir in the combination is between 50:1 to 1:1, thereby treating the SARS CoV-2 infection in the cell or subject.

63. A method of reducing the toxicity of an antiviral agent in a cell or subject, comprising administering a combination of a hypericin compound and the antiviral agent to the subject, wherein the molar amount of the hypericin compound in the combination is greater than the molar amount of the antiviral agent, thereby reducing the toxicity of the antiviral agent in the cell or subject.

64. The method of embodiment 63, wherein the reducing the toxicity is relative to the toxicity of the antiviral agent in the cell or subject when provided in the absence of the hypericin compound.

65. The method of any one of embodiments 63-64, wherein the efficacy of the combination is greater than:

(i) the efficacy of the hypericin compound alone at the molar amount used in the combination; or (ii) the efficacy of the antiviral agent alone at the molar amount used in the combination.

66. The method of embodiment 65 comprising (i).

67. The method of embodiment 65, comprising (ii).

68. The method of any one of embodiments 63-67, wherein the efficacy of the combination is at least $X_1$-fold greater than the efficacy of the hypericin compound alone at the molar amount used in the combination, wherein $X_1$ is 1, 1.25, 1.5, 1.75, 2, 2.5, or greater.

69. The method of any one of embodiments 63-68, wherein the efficacy of the combination is at least $X_1$-fold greater than the efficacy of the antiviral agent alone at the molar amount used in the combination, wherein $X_1$ is 1, 1.25, 1.5, 1.75, 2, 2.5, or greater.

70. The method of any one of embodiments 63-69, wherein the toxicity of the antiviral agent in the cell or subject is reduced upon administration of the antiviral agent in combination with a hypericin compound between 1% and 50%, e.g., compared with the toxicity of the antiviral agent when administered in the absence of the hypericin compound.

71. The method of any one of embodiments 63-70, wherein the molar amount of the hypericin compound in the combination comprises the molar concentration of the hypericin compound in the combination.

72. The method of any one of embodiments 63-71, wherein the molar amount of the antiviral agent in the combination comprises the molar concentration of the antiviral agent in the combination.

73. The method of any one of embodiments 63-72, wherein each of the hypericin compound and the antiviral agent is independently formulated as a pharmaceutical composition.

74. The method of any one of embodiments 63-72, wherein the hypericin compound and the antiviral agent are formulated together as a pharmaceutical composition.

75. The method of any one of embodiments 63-74, wherein each of the hypericin compound and the antiviral agent is provided (e.g., administered) concomitantly to the subject.

76. The method of any one of embodiments 63-74, wherein each of the hypericin compound and the antiviral agent is provided (e.g., administered) sequentially to the subject.

77. The method of embodiment 76, wherein the hypericin compound is provided (e.g., administered) to the subject prior to the antiviral agent.

78. The method of embodiment 76, wherein the antiviral agent is provided (e.g., administered) to the subject prior to the hypericin compound.

79. The method of any one of embodiments 63-78, wherein the hypericin compound is a compound of Formula (I):

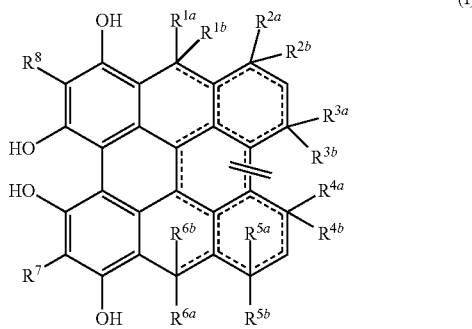

or a pharmaceutically acceptable salt thereof, wherein:

each of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C^6$ heteroalkyl, halo, cyano, —$OR^A$, —$NR^BR^C$, —$C(O)NR^BR^C$, or heterocyclyl, wherein each alkyl, alkenyl, alkynyl, haloalkyl, heteroalkyl, cycloalkyl, and heterocyclyl is optionally substituted with one or more $R^9$; or $R^{1a}$ and $R^{1b}$, $R^{2a}$ and $R^{2b}$, $R^{3a}$ and $R^{3b}$, $R^{4a}$ and $R^{4b}$, $R^{5a}$ and $R^{5b}$, or $R^{6a}$ and $R^{6b}$ is independently taken together with the atoms to which they are attached to form an oxo group;

each of $R^7$ and $R^8$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^{10}$;

each of $R^A$, $R^B$, $R^c$, and $R^D$ is hydrogen, $C_1$-$C_6$ alkyl, $C_1$-$C_6$ haloalkyl, $C_1$-$C_6$ heteroalkyl, cycloalkyl, or heterocyclyl;

each of $R^9$ and $R^{10}$ is independently $C_1$-$C_6$ alkyl, $C_1$-$C_6$ haloalkyl, $C_1$-$C_6$ heteroalkyl, halo, or cyano;

the bond indicated by "=" is either present or absent, wherein if the bond is absent, the corresponding carbon atoms are independently attached to hydrogen, $C_1$-$C_6$ alkyl, or halo; and each "═" is independently a single or double bond, according to valency.

80. The method of embodiment 79, wherein $R^{1a}$ and $R^{1b}$ are taken together to form an oxo group.

81. The method of any one of embodiments 79-80, wherein one of $R^{2a}$ and $R^{2b}$ is —$OR^A$ (e.g.,—OH) and the other of $R^{2a}$ and $R^{2b}$ is hydrogen.

82. The method of any one of embodiments 79-81, wherein $R^{6a}$ and $R^{6b}$ are taken together to form an oxo group.

83. The method of any one of embodiments 79-82, wherein one of $R^{5a}$ and $R^{5b}$ is —$OR^A$ (e.g., —OH) and the other of $R^{5a}$ and $R^{5b}$ is hydrogen.

84. The method of any one of embodiments 63-83, wherein the hypericin compound is prepared synthetically or is extracted from a natural source (e.g., St. John's Wort).

85. The method of embodiment 84, wherein the hypericin compound is prepared synthetically.

86. The method of embodiment 84, wherein the hypericin compound is extracted from a natural source (e.g., St. John's Wort).

87. The method of any one of embodiments 63-86, wherein the hypericin compound is a compound selected from Table 1 or a pharmaceutically acceptable salt thereof 88. The method of embodiment 87, wherein the hypericin compound is substantially pure.

89. The method of any one of embodiments 87-88, wherein the hypericin compound is provided as a pharmaceutical composition and the pharmaceutical composition comprises less than about 50%, 55%, 60%, 65%, 70%, 75%, 80%, 85%, 90%, 95%, 99%, or 99.9% of another compound.

90. The method of any one of embodiments 87-89, wherein the hypericin compound is provided as a pharmaceutical composition and the pharmaceutical composition comprises less than about 50%, 55%, 60%, 65%, 70%, 75%, 80%, 85%, 90%, 95%, 99%, or 99.9% of another compound listed in Table 1 or a pharmaceutically acceptable salt thereof.

91. The method of any one of embodiments 87-89, wherein the hypericin compound is provided as a pharmaceutical composition and the pharmaceutical composition comprises less than about 50%, 55%, 60%, 65%, 70%, 75%, 80%, 85%, 90%, 95%, 99%, or 99.9% of a compound present in St. John's Wort.

92. The method of any one of embodiments 63-91, wherein the hypericin compound is provided in the combination in the absence of hyperforin, adhyperforin, or a pharmaceutically acceptable salt thereof.

93. The method of any one of embodiments 63-92, wherein the hypericin compound is hypericin or a pharmaceutically acceptable salt thereof.

94. The method of embodiment 93, wherein the hypericin or a pharmaceutically acceptable salt thereof is provided in the combination in the absence of hyperforin, adhyperforin, or a pharmaceutically acceptable salt thereof.

95. The method of any one of embodiments 93-94, wherein the hypericin or a pharmaceutically acceptable salt thereof is provided as a pharmaceutical composition, and the pharmaceutical composition comprises less than about 90%, 95%, 99%, or 99.9% of another compound in listed in Table 1 or a pharmaceutically acceptable salt thereof.

96. The method of any one of embodiments 63-95, wherein the antiviral agent is a small molecule, antibody, peptide, or oligonucleotide.

97. The method of any one of embodiments 63-96, wherein the antiviral agent is an agent that modulates a step in the viral life cycle.

98. The method of any one of embodiments 63-97, wherein the antiviral agent selected from an attachment inhibitor, post-attachment inhibitor, fusion inhibitor, entry inhibitor, uncoating inhibitor, protease inhibitor, polymerase inhibitor, nucleotide reverse transcriptase inhibitor, nucleoside reverse transcriptase inhibitor, non-nucleoside reverse transcriptase inhibitor, and integrase inhibitor.

99. The method of any one of embodiments 63-98, wherein the antiviral agent is a nucleoside analog or a non-ribosomal peptide.

100. The method of any one of embodiments 63-98, wherein the antiviral agent is compound of Formula (II):

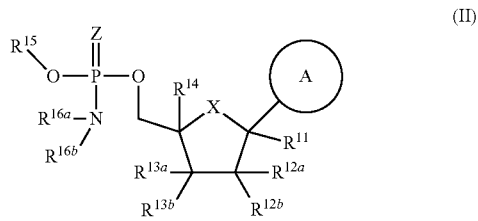

(II)

or a pharmaceutically acceptable salt thereof, wherein:

Ring A is a heteroaryl or heterocyclyl, each of which is optionally substituted with $R^{17}$ (e.g., a nucleobase or analog thereof);

X is O or NR';

Z is O or S;

each of $R^{11}$ and $R^{14}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, or cyano;

each of $R^{12a}$, $R^{12b}$, $R^{13a}$, is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —C(O)$NR^BR^C$—$NR^BC(O)R^D$, cycloalkyl, heterocyclyl, aryl, or heteroaryl, wherein each alkyl, alkenyl, alkynyl, haloalkyl, heteroalkyl, cycloalkyl, heterocyclyl, aryl, and heteroaryl is optionally substituted with one or more $R^{17}$; or $R^{15}$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, aryl, heteroaryl, cycloalkyl, or heterocyclyl, wherein each alkyl, cycloalkyl, and heterocyclyl is optionally substituted with one or more $R'^7$;

each of $R^{16a}$ and $R^{16b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, —C(O)$R^D$, —$C_1$-$C_6$ alkylene-C(O)O-$C_1$-$C_6$ alkyl, —$C_1$-$C_6$ alkylene-C(O)-$C_1$-$C_6$ alkenyl, —$C_1$-$C_6$ alkylene-C(O)O-$C_1$-$C_6$ heteroalkyl, —$C_1$-$C_6$ alkylene-C(O)O-$C_1$-$C_6$ haloalkyl, —$C_1$-$C_6$ alkylene-C(O)O-$C_1$-$C_6$ cycloalkyl, —$C_1$-$C_6$ alkylene-C(O)O-$C_1$-$C_6$ heterocyclyl, cycloalkyl, or heterocyclyl, wherein each alkyl, alkylene, alkenyl, alkynyl, haloalkyl, heteroalkyl, cycloalkyl, and heterocyclyl is optionally substituted with one or more $R^{18}$;

R' is hydrogen or $C_1$-$C_6$ alkyl;

each of $R^A$, $R^B$, $R^C$, and $R^D$ is hydrogen, $C_1$-$C_6$ alkyl, $C_1$-$C_6$ haloalkyl, $C_1$-$C_6$ heteroalkyl, cycloalkyl, or heterocyclyl; and each of $R^{17}$ and $R^{18}$ is independently $C_1$-$C_6$ alkyl, $C_1$-$C_6$ haloalkyl, $C_1$-$C_6$ heteroalkyl, halo, or cyano.

101. The method of any one of embodiments 63-100, wherein the antiviral agent targets an RNA virus.

102. The method of any one of embodiments 63-101, wherein the antiviral agent is selected from remdesivir, sofosbuvir, or a pharmaceutically acceptable salt thereof.

103. The method of any one of embodiments 63-102, wherein the antiviral agent is selected from remdesivir or a pharmaceutically acceptable salt thereof.

104. The method of any one of embodiments 63-103, wherein the hypericin compound is administered at a dosage to provide a concentration of between 0.1 μM and 500 μM in a subject or cell.

105. The method of any one of embodiments 63-104, wherein the hypericin compound is administered at a dosage to provide a concentration of between 1 μM and 25 μM in a subject or cell.

106. The method of any one of embodiments 63-105, wherein the antiviral agent (e.g., remdesivir) is administered at a dosage to provide a concentration of between 0.01 μM and 25 μM in a subject or cell.

107. The method of any one of embodiments 63-106, wherein the antiviral agent (e.g., remdesivir) is administered at a dosage to provide a concentration of between 0.1 μM and 5 μM in a subject or cell.

108. The method of any one of embodiments 63-107, wherein the ratio of the amount of hypericin compound to the antiviral agent in the combination is between 200:1 to 1:1.

109. The method of embodiment 108, wherein the ratio of the amount of hypericin compound to the antiviral agent in the combination is between 50:1 to 1:1.

110. The method of any one of embodiments 108-109, wherein the ratio of the amount of hypericin compound to the antiviral agent in the combination is between 25:1 to 2:1.

111. The method of any one of embodiments 63-110, wherein:

(i) the hypericin compound is hypericin or a pharmaceutically acceptable salt thereof;

(ii) the antiviral agent is remdesivir or a pharmaceutically acceptable salt thereof; and (iii) the molar amount of the hypericin compound in the combination is between 20-fold and 5-fold greater than the molar amount of the antiviral agent (e.g., remdesivir).

112. The method of any one of embodiments 63-111, further comprising administration of an additional agent.

113. The method of any one of embodiments 63-112, wherein the subject is a mammal (e.g., a human).

114. The method of any one of embodiments 63-113, wherein the cell comprises an angiotensin-converting enzyme 2 (ACE2) receptor on the cell surface.

115. The method of any one of embodiments 63-114, wherein the cell is a cell present in the respiratory system, nervous system, gastrointestinal system, circulatory system, endocrine system, immune system, or excretory system.

116. The method of any one of embodiments 63-115, wherein the cell is a bronchial cell, renal cell, enterocyte, goblet cell, skin cell, islet cell, neuronal cell, glial cell, or heart cell.

117. The method of any one of embodiments 63-116, wherein the cell or subject is infected with a viral infection.

118. The method of embodiment 117, wherein the viral infection is a SARS coronavirus (SARS-CoV), MERS coronavirus (MERS-CoV), or SARS-CoV-2 infection.

119. The method of any one of embodiments 63-118, wherein the viral infection is a SARS CoV-2 infection.

120. A method of reducing the toxicity of remdesivir in a cell or subject, comprising providing a combination of (i) hypericin or a pharmaceutically acceptable salt thereof and (ii) remdesivir or a pharmaceutically acceptable salt thereof to the cell or subject,
wherein of the molar ratio of hypericin to remdesivir in the combination is between 50:1 to 1:1,
thereby reducing the toxicity of remdesivir in the cell or subject.

121. The method of embodiment 120, wherein of the molar ratio of hypericin to remdesivir in the combination is between 50:1 to 2:1.

122. A method of reducing the virulence of a virus in a subject, comprising administering a combination of a hypericin compound and remdesivir to the subject,
wherein the amount of the hypericin compound and the amount of remdesivir are selected such that the molar concentration of the hypericin compound is greater than the molar concentration of remdesivir;
whereby the virulence of the virus is reduced in the subject.

123. The method of embodiment 122, wherein reducing the virulence comprises one or more of:
(i) reducing the infection rate;
(ii) reducing the doubling rate, e.g., amount of virus produced by an infected host cell;
(iii) reducing the rate of viral DNA/RNA synthesis;
(iv) reducing the rate of DNA/RNA mutations by a nucleic acid polymerase;
(v) reducing the rate of virion packaging.

124. A method of treating a SARS CoV-2 infection in a human subject, comprising providing a combination of (i) hypericin or a pharmaceutically acceptable salt thereof and (ii) remdesivir or a pharmaceutically acceptable salt thereof to human subject, wherein:
the molar ratio of hypericin to remdesivir in the combination is between 25:1 to 2:1, and
the hypericin is provided in the combination in the absence of hyperforin, adhyperforin, or a pharmaceutically acceptable salt thereof;
thereby treating the SARS CoV-2 infection in human subject.

125. A method of reducing the effective antiviral dose of remdesivir in a cell or subject, comprising administering a combination of: (i) hypericin or a pharmaceutically acceptable salt thereof; and (ii) remdesivir or a pharmaceutically acceptable salt thereof, to the cell or subject,
wherein the molar amount of the hypericin compound in the combination is greater than the molar amount of remdesivir,
thereby reducing the effective antiviral dose of remdesivir in the cell or subject.

126. A method of improving the efficacy of remdesivir in a cell or subject for the treatment of SARS CoV-2, comprising administering a combination of: (i) hypericin or a pharmaceutically acceptable salt thereof; and (ii) remdesivir or a pharmaceutically acceptable salt thereof, to the cell or subject,
wherein the molar amount of the hypericin compound in the combination is greater than the molar amount of remdesivir,
thereby improving the efficacy of remdesivir in the cell or subject.

127. The method of any one of embodiments 120-126, wherein the efficacy of the combination is greater than:
(i) the efficacy of the hypericin compound alone at the amount used in the combination; or
(ii) the efficacy of the antiviral agent alone at the amount used in the combination.

128. The method of embodiment 127, comprising (i).

129. The method of embodiment 127, comprising (ii).

130. The method of any one of embodiments 120-129, wherein the efficacy of the combination is at least $X_1$ greater than the efficacy of the hypericin compound alone at the amount used in the combination, wherein $X_1$ is 1, 1.25, 1.5, 1.75, 2, 2.5, or greater.

131. The method of any one of embodiments 120-130, wherein the efficacy of the combination is at least $X_1$ greater than the efficacy of the antiviral agent alone at the amount used in the combination, wherein Xi is 1, 1.25, 1.5, 1.75, 2, 2.5, or greater.

132. The method of any one of embodiments 120-131, wherein the hypericin compound is a compound of Formula (I):

or a pharmaceutically acceptable salt thereof, wherein:
each of $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^9$; or
$R^{1a}$ and $R^{1b}$, $R^{2a}$ and $R^{2b}$, $R^{3a}$ and $R^{3b}$, $R^{4a}$ and $R^{4b}$, $R^{5a}$ and $R^{5b}$, $R^{6a}$ or $R^{6b}$ is independently taken together with the atoms to which they are attached to form an oxo group;
each of $R^7$ and $R^8$ is independently hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, halo, cyano, —$OR^A$, —$NR^BR^C$, —$C(O)NR^BR^C$, —$NR^BC(O)R^D$, cycloalkyl, or heterocyclyl, wherein each alkyl, alkenyl, alkynyl, haloalkyl, heteroalkyl, cycloalkyl, and heterocyclyl is optionally substituted with one or more $R^m$;

each of $R^A$, $R^B$, $R^C$, and $R^D$ is hydrogen, $C_1$-$C_6$ alkyl, $C_1$-$C_6$ haloalkyl, $C_1$-$C_6$ heteroalkyl, cycloalkyl, or heterocyclyl;

each of $R^9$ and $R^{10}$ is independently $C_1$-$C_6$ alkyl, $C_1$-$C_6$ haloalkyl, $C_1$-$C_6$ heteroalkyl, halo, or cyano;

the bond indicated by "=" is either present or absent, wherein if the bond is absent, the corresponding carbon atoms are independently attached to hydrogen, $C_1$-$C_6$ alkyl, or halo; and each "===" is independently a single or double bond, according to valency.

133. The method of embodiment 132, wherein $R^{1a}$ and $R^{1b}$ are taken together to form an oxo group.

134. The method of any one of embodiments 132-133, wherein one of $R^{2a}$ and $R^{2b}$ is —$OR^A$ (e.g., —OH) and the other of $R^{2a}$ and $R^{2b}$ is hydrogen.

135. The method of any one of embodiments 132-134, wherein $R^{6a}$ and $R^{6b}$ are taken together to form an oxo group.

136. The method of any one of embodiments 132-135, wherein one of $R^{5a}$ and $R^{5b}$ is —$OR^A$ (e.g., —OH) and the other of $R^{5a}$ and $R^{5b}$ is hydrogen.

137. The method of any one of embodiments 120-136, wherein the hypericin compound is a compound selected from Table 1 or a pharmaceutically acceptable salt thereof 138. The method of any one of embodiments 120-137, wherein the hypericin compound is hypericin or a pharmaceutically acceptable salt thereof.

139. The method of any one of embodiments 120-138, wherein the hypericin compound is administered at a dosage to provide a concentration of between 0.1 µM and 500 µM in a subject or cell.

140. The method of any one of embodiments 120-139, wherein the hypericin compound is administered at a dosage to provide a concentration of between 1 µM and 25 µM in a subject or cell.

141. The method of any one of embodiments 120-140, wherein the remdesivir is administered at a dosage to provide a concentration of between 0.01 µM and 25 µM in a subject or cell.

142. The method of any one of embodiments 120-141, wherein the remdesivir is administered at a dosage to provide a concentration of between 0.1 µM and 5 µM in a subject or cell.

143. The method of any one of embodiments 120-142, wherein:
(i) the hypericin compound is hypericin or a pharmaceutically acceptable salt thereof;
(ii) the molar concentration of the hypericin compound is between 5-fold and 10-fold greater than the molar concentration of the remdesivir.

144. The method of any one of embodiments 120-143, wherein each of the hypericin compound and the remdesivir is independently formulated as a pharmaceutical composition.

145. The method of any one of embodiments 120-144, wherein the hypericin compound and the remdesivir are formulated together as a pharmaceutical composition.

146. The method of any one of embodiments 120-145, wherein each of the hypericin compound and the remdesivir is administered concomitantly.

147. The method of any one of embodiments 120-145, wherein each of the hypericin compound and the remdesivir is administered sequentially.

148. The method of embodiment 147, wherein the hypericin compound is administered prior to the remdesivir.

149. The method of embodiment 147, wherein the remdesivir is administered prior to the hypericin compound.

150. The method of any one of embodiments 120-149, further comprising administration of an additional agent.

151. The method of any one of embodiments 120-150, wherein the subject is a mammal.

152. The method of any one of embodiments 120-151, wherein the subject is a human.

EXAMPLES

The following examples are provided to further illustrate some embodiments of the present disclosure but are not intended to limit the scope of the disclosure. It will be understood by their exemplary nature that other procedures, methodologies, or techniques known to those skilled in the art may alternatively be used.

Example 1: Anti-viral Activity of Exemplary Compounds

This example demonstrates the ability of hypericin compounds disclosed herein to act in combination with known an exemplary antiviral agent (e.g., remdesivir) to decrease viral infection-induced cytotoxicity and viral replication of the novel SARS-CoV-2 coronavirus in a model cell line. In particular, the ability of the hypericin compounds to synergize with remdesivir at a sub-therapeutic dose of remdesivir (0-2.5 µM) to achieve an increase in cell viability over time in cells infected with SARS-CoV-2.

Vero E6 cells were seeded at 25,000 cells/well in 96-well plates and SARS-CoV-2 was added into the wells at a MOI of 0.01. After 1 hour, hypericin (Cayman Chemical, ≥95% purity) was added into the wells at final concentrations of 1.5625-100 µM or the vehicle only control (DMSO), followed by the addition of remdesivir (Novation Chemicals, 98% purity) at final concentrations of 0.3125-5 µM or the vehicle only control (DMSO), and incubated at 37° C.

After 72 hours of incubation, host cell viability was assessed using CellTiter-Glo® Luminescent Cell Viability Assay (Promega) according to the manufacturer's instructions. Results were normalized to the highest dose of remdesivir alone (5 µM) and are summarized below in Table 1. As shown, remdesivir (5 µM) alone dose-dependently improved host cell viability of SARS-CoV-2-infected Vero E6 cells as expected. Similarly, hypericin (25-50 µM) alone enabled modest improvements in host cell viability.

However, hypericin demonstrated an improved anti-viral effect when administered in combination with remdesivir. For example, remdesivir (1.25 µM) combined with hypericin (6.25 -50µM) improved host cell viability up to >64%, compared to remdesivir (1.25 µM) alone which only had host cell viability of 26% (Table 2). When combined with varying amounts of hypericin, it was shown that lower concentrations of remdesivir were effective at improving host cell viability (e.g., 1.25 µM exhibited 26-29% host cell viability).

Similarly, remdesivir can increase the efficacy of hypericin. Hypericin alone (12.5-100 µM) alone enabled modest improvements in host cell viability up to 62% at 50 µM. For example, remdesivir (0.3125-2.5 µM) can combine with hypericin (12.5-50 µM) to increase viability to 70-76%, compared to the 20-62% viability seen at 12.5-50 µM of hypericin alone.

TABLE 2

Cell viability assay to assess impact of hypericin and remdesivir combinations on SARS-CoV2 infection on Vero E6 host cells.

| | | Remdesivir concentration [µM] | | | | | |
|---|---|---|---|---|---|---|---|
| | | 5 | 2.5 | 1.25 | 0.625 | 0.3125 | 0 |
| Hypericin concentration [µM] | 100 | 39.3 | 43.7 | 43.63 | 43.6 | 43.7 | 38.0 |
| | 50 | 55.2 | 61.6 | 62.0 | 62.2 | 62.5 | 62.6 |
| | 25 | 64.5 | 71.0 | 72.7 | 73.7 | 70.4 | 62.0 |
| | 12.5 | 71.4 | 75.1 | 76.4 | 72.3 | 53.7 | 20.4 |
| | 6.25 | 71.1 | 69.5 | 66.0 | 32.1 | 19.3 | 12.8 |
| | 3.125 | 79.0 | 70.0 | 28.3 | 18.0 | 15.7 | 12.9 |
| | 1.563 | 90.8 | 52.9 | 26.0 | 18.3 | 16.4 | 14.6 |
| | 0 | 100 | 38.1 | 25.2 | 21.9 | 19.8 | 17.5 |

Figure 2:
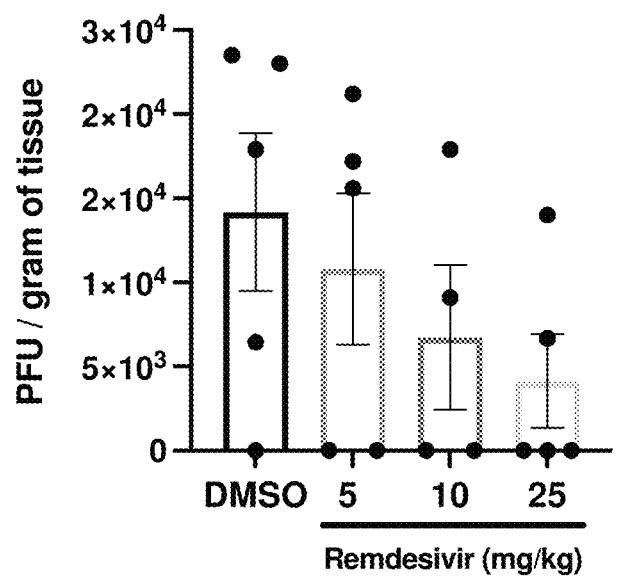
FIG. 2 is a graph depicting the dose-dependent effect of remdesivir on reducing infectious viral titers in SARS-CoV-2 infected mice on day 4 post-infection.

Next, median tissue culture infectious dose (TCID50) assay was used to assess the viral titer in treated cells. Remdesivir alone dose-dependently reduced viral titers of SARS-CoV-2 to zero TCID50/mL, compared to control conditions without Remdesivir which maintained viral titers around 10^6 TCID50/mL (FIG. 2). Remdesivir combined with hypericin further decreased viral titers. For example, remdesivir (0-2.5 µM) combined with hypericin (3.125-50 µM) led to an equivalent reduction in viral titer compared to remdesivir (5 µM) alone. Furthermore, remdesivir (0-5 µM) combined with hypericin (3.125-50 µM) further reduced viral titers to zero.

Example 2: Anti-viral Activity of Remdesivir in SARS-CoV-2 Infected Mice

B6.Cg-Ceslctml.lLoc/J mice were infected with 1×10^5 particles of SARS-CoV-2 virus [B.1.351] via intranasal administration. Mice were treated daily with vehicle or with remdesivir (5, 10 or 25 mg/kg) intraperitoneally starting day 1 post infection. At day 4 post infection, all mice were euthanized. At that time point, lungs were collected and stored at −80° C. Lung tissues were processed for determination of infectious titers (plaque forming unit per mg of tissues). The results are summarized in FIG. 2. As expected, remdesivir demonstrated a dose-dependent effect on reducing infectious titers, with 25 mg/kg having the strongest antiviral effect in reducing infectious titer.

Example 3: Anti-viral Activity of Remdesivir and Hypericin in SARS-CoV Infected Mice In this example, the efficacy and safety/tolerability of hypericin and remdesivir were investigated in mice infected with SARS CoV-2 virus. In brief, mice (10-12 weeks old) were infected with 1×10^5 particles of SARS-CoV-2 virus [B.1.351] via intranasal administration. For mice receiving hypericin, the mice were pre-treated with hypericin starting two days prior to infection. Post-infection, the mice were administered remdesivir or other treatment starting day 1 post infection daily via IP as follows: (1) negative vehicle control (saline), (2) Remdesivir (25 mg/kg), (3) Remdesivir (10 mg/kg), (4) Hypericin (20 mg/kg), (5) Hypericin (20 mg/kg)+Remdesivir (10 mg/kg). Each group contained 7 mice. Survival, body weight, temperature, and scoring (symptoms, disease features, etc.) of mice were tracked and monitored daily. At day 4 post infection, all mice were euthanized. At that time point, tissues (lung) as well as serum were collected and stored at −80° C. Pieces of lung, heart, and brain tissues were also fixed in in PFA (4%). Lung tissues were processed for determination of infectious titers (plaque forming unit per mg of tissues).

Figure 3:
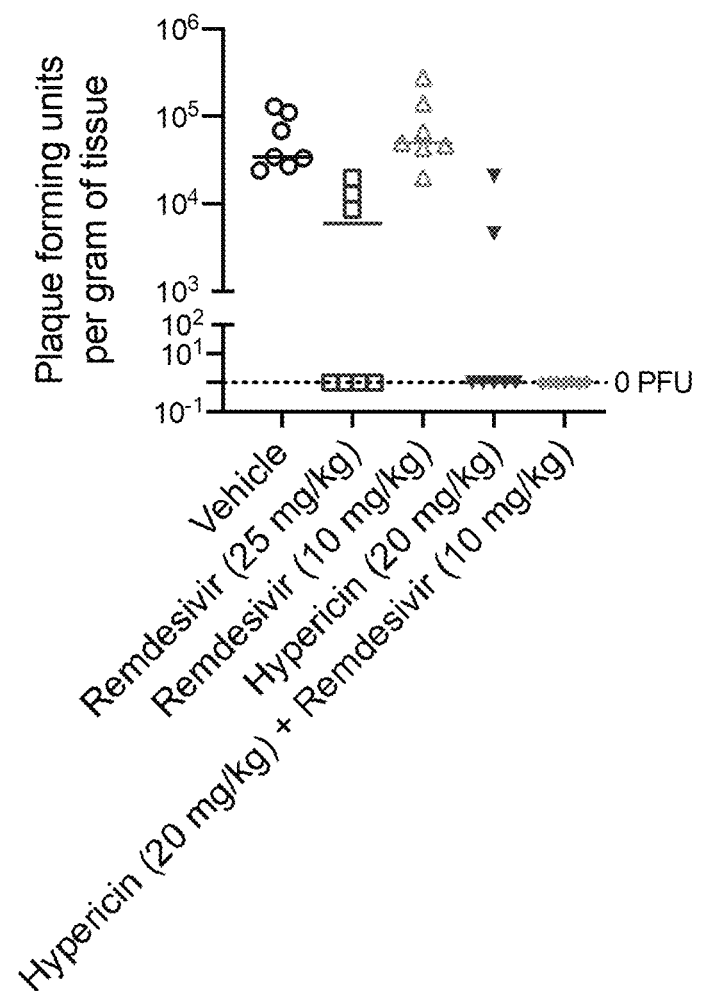
FIG. 3 is graph depicting the infectious titers in lungs of SARS-CoV-2 infected mice pre-treated with hypericin alone or in combination with remdesivir on day 4 post-infection.
Figure 4A:
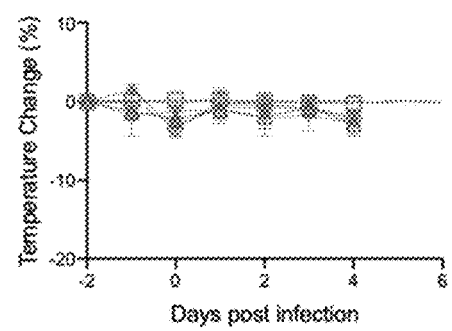
FIGS. 4A-4D are graphs illustrating safety and tolerability assessments of SARS-CoV-2 infected mice pre-treated with hypericin along or in combination with remdesivir on day 4 post-infection.
Figure 4B:
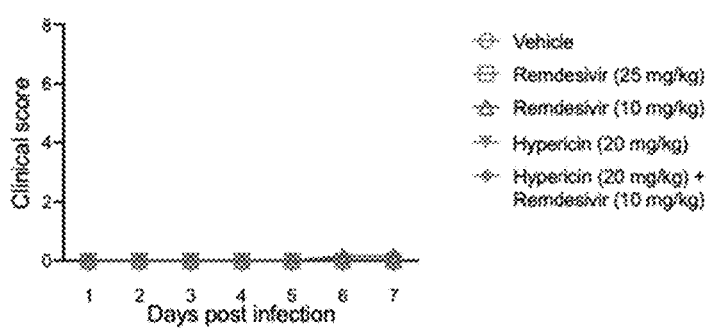
Figure 4C:
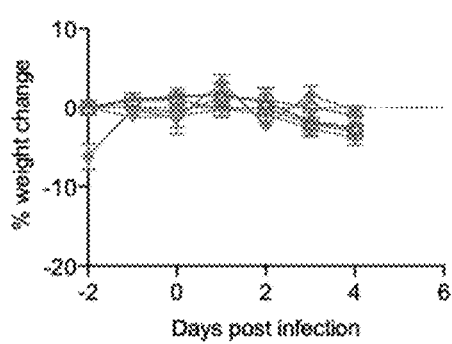
Figure 4D:
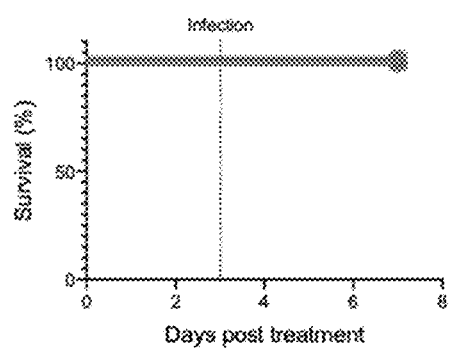

At day 4 post-infection, high-dose Remdesivir (25 mg/kg) eliminated all infectious titers in 4 out of 7 mice. Low-dose Remdesivir (10 mg/kg) did not impact infectious titers compared to vehicle. Hypericin (20 mg/kg) eliminated all infectious titers in 5 out of 7 mice alone. Hypericin (20 mg/kg)+low-dose Remdesivir (10 mg/kg) eliminated all infectious titers in all 7 out of 7 mice (FIG. 3). All compounds and combinations demonstrated unremarkable safety and tolerability, as demonstrated in FIGS. 4A-4D.

INCORPORATION BY REFERENCE AND EQUIVALENTS

The entire contents of all patents, published applications, and references cited herein are incorporated by reference in their entirety. While example embodiments have been particularly shown and described, it will be understood by those skilled in the art that various changes in form and details may be made therein without departing from the scope of the embodiments encompassed by the appended claims.

The invention claimed is:

1. A method of treating a SARS CoV-2 infection in a human subject, comprising administering a combination of (i) hypericin or a pharmaceutically acceptable salt thereof and (ii) remdesivir or a pharmaceutically acceptable salt thereof to the human subject,
   wherein the molar amount of the hypericin or a pharmaceutically acceptable salt thereof in the combination is greater than the molar amount of remdesivir or a pharmaceutically acceptable salt thereof,
   thereby treating the SARS CoV-2 infection in the human subject.

2. The method of claim 1, wherein the molar ratio of hypericin or a pharmaceutically acceptable salt thereof to remdesivir or a pharmaceutically acceptable salt thereof in the combination is between 50:1 to 2:1.

3. The method of claim 1, wherein the molar ratio of hypericin or a pharmaceutically acceptable salt thereof to remdesivir or a pharmaceutically acceptable salt thereof in the combination is between 25:1 to 2:1.

4. The method of claim 1, wherein the hypericin or a pharmaceutically acceptable salt thereof is prepared synthetically or is extracted from a natural source.

5. The method of claim 1, wherein the hypericin or a pharmaceutically acceptable salt thereof is provided in the combination in the absence of hyperforin, adhyperforin, or a pharmaceutically acceptable salt thereof.

6. The method of claim 1, further comprising administration of an additional agent.

7. The method of claim 6, wherein the additional agent is selected from an immune therapy, a vaccine, an anti-inflammatory agent, a pain reliever, a mucolytic agent, a cancer therapy, an antiviral agent, an antifungal agent, an antibacterial agent, a bronchodilator, and a vasodilator.

8. The method of claim 1, wherein the human subject is diagnosed with CoVID-19.

9. The method of claim 1, wherein the SARS CoV-2 infection is present within a virally infected organ, tissue, or cell in the human subject.

10. The method of claim 9, wherein the virally infected tissue is selected from lung tissue, tracheal tissue, intestinal tissue, skin tissue, pancreatic tissue, vascular tissue, mucosal tissue, kidney tissue, brain tissue, nervous tissue, and cardiac tissue.

11. The method of claim 9, wherein the virally infected cell comprises an angiotensin-converting enzyme 2 (ACE2) receptor on the cell surface.

12. The method of claim 1, wherein each of hypericin or a pharmaceutically acceptable salt thereof and remdesivir or a pharmaceutically acceptable salt thereof is independently formulated as a pharmaceutical composition.

13. The method of claim 1, wherein each of hypericin or a pharmaceutically acceptable salt thereof and remdesivir or a pharmaceutically acceptable salt thereof is formulated together as a single pharmaceutical composition.

14. The method of claim 1, wherein each of hypericin or a pharmaceutically acceptable salt thereof and remdesivir or a pharmaceutically acceptable salt thereof is administered concomitantly to the human subject.

15. The method of claim 1, wherein each of hypericin or a pharmaceutically acceptable salt thereof and remdesivir or a pharmaceutically acceptable salt thereof is administered sequentially to the human subject.

16. The method of claim 1, wherein the efficacy of the combination of hypericin or a pharmaceutically acceptable salt thereof and remdesivir or a pharmaceutically acceptable salt thereof is at least $X_1$-fold greater than the efficacy of the hypericin alone at the molar amount used in the combination, wherein $X_1$ is 1, 1.25, 1.5, 1.75, 2, 2.5, or greater.

17. A method of treating a SARS CoV-2 infection in a human subject, comprising administering a combination of (i) hypericin or a pharmaceutically acceptable salt thereof and (ii) remdesivir or a pharmaceutically acceptable salt thereof to the human subject, wherein:

the molar ratio of hypericin or a pharmaceutically acceptable salt thereof to remdesivir or a pharmaceutically acceptable salt thereof in the combination is between 25:1 to 2:1, and the hypericin is provided in the combination in the absence of hyperforin, adhyperforin, or a pharmaceutically acceptable salt thereof;

thereby treating the SARS CoV-2 infection in the human subject.

18. A method of reducing the effective antiviral dose of remdesivir in a human subject, comprising administering a combination of: (i) hypericin or a pharmaceutically acceptable salt thereof; and (ii) remdesivir or a pharmaceutically acceptable salt thereof, to the human subject, wherein the molar amount of the hypericin or a pharmaceutically acceptable salt thereof in the combination is greater than the molar amount of remdesivir or a pharmaceutically acceptable salt thereof, thereby reducing the effective antiviral dose of remdesivir in the human subject.

* * * * *